United States Patent
Selig et al.

(10) Patent No.: US 7,169,369 B2
(45) Date of Patent: Jan. 30, 2007

(54) METHOD AND DEVICE FOR DEACTIVATING ITEMS AND FOR MAINTAINING SUCH ITEMS IN A DEACTIVATED STATE

(75) Inventors: Victor Selig, Euclid, OH (US); Karl F. Ludwig, Girard, PA (US); Jude A. Kral, Twinsburg, OH (US); Christopher A. Jethrow, Maple Heights, OH (US); Jeffrey Horacek, Mentor, OH (US); Donald A. Sargent, Wickliffe, OH (US)

(73) Assignee: Steris Inc., Temecula, CA (US)

( * ) Notice: Subject to any disclaimer, the term of this patent is extended or adjusted under 35 U.S.C. 154(b) by 418 days.

(21) Appl. No.: 10/633,348

(22) Filed: Aug. 1, 2003

(65) Prior Publication Data
US 2005/0025685 A1    Feb. 3, 2005

(51) Int. Cl.
*A61L 2/00*    (2006.01)
(52) U.S. Cl. ............... 422/292; 422/300; 206/438
(58) Field of Classification Search .......... 422/292, 422/297, 300; 206/438, 439
See application file for complete search history.

(56) References Cited

U.S. PATENT DOCUMENTS

| | | | |
|---|---|---|---|
| 3,717,434 A | 2/1973 | Black | 21/94 |
| 4,731,222 A | 3/1988 | Kralovic et al. | 422/37 |
| 4,783,321 A * | 11/1988 | Spence | 422/300 |
| 4,892,706 A | 1/1990 | Kralovic et al. | 422/28 |
| 4,919,888 A * | 4/1990 | Spence | 422/26 |
| 5,077,008 A | 12/1991 | Kralovic et al. | 422/37 |
| 5,091,343 A | 2/1992 | Schneider et al. | 422/297 |
| 5,116,575 A | 5/1992 | Badertscher et al. | 422/28 |
| 5,217,698 A | 6/1993 | Siegel et al. | 422/295 |
| 5,290,511 A | 3/1994 | Newman | 422/26 |
| 5,346,075 A | 9/1994 | Nichols et al. | 211/60.1 |
| 5,439,654 A | 8/1995 | Kochte | 422/292 |
| 5,529,750 A | 6/1996 | Kochte | 422/28 |
| 5,534,221 A | 7/1996 | Hillebrenner et al. | 422/33 |
| 5,641,065 A * | 6/1997 | Owens et al. | 206/370 |
| 5,711,921 A | 1/1998 | Langford | 422/292 |
| 5,753,195 A | 5/1998 | Langford et al. | 422/292 |
| 5,906,802 A | 5/1999 | Langford | 422/300 |
| 6,343,612 B1 * | 2/2002 | Dahl | 134/117 |
| 6,528,017 B2 | 3/2003 | Jacobs et al. | 422/33 |
| 6,596,232 B1 | 7/2003 | Lin et al. | 422/28 |
| 2004/0105780 A1 | 6/2004 | Lin et al. | 422/28 |
| 2005/0025685 A1 | 2/2005 | Selig et al. | 422/292 |

* cited by examiner

*Primary Examiner*—Krisanne Jastrzab
*Assistant Examiner*—Sean E. Conley
(74) *Attorney, Agent, or Firm*—Kusner & Jaffe; Michael A. Centanni

(57) ABSTRACT

A reprocessor for microbially deactivating items. The reprocessor has a circulation system for circulating a microbial deactivation fluid through a deactivation chamber that forms part of the circulation system. A container is provided for insertion into the deactivation chamber for holding items to be microbially deactivated. The container includes a tray and a lid. The tray and lid have interlocking, integrally formed, rigid seal elements formed thereon to form a seal between the tray and the lid.

14 Claims, 19 Drawing Sheets

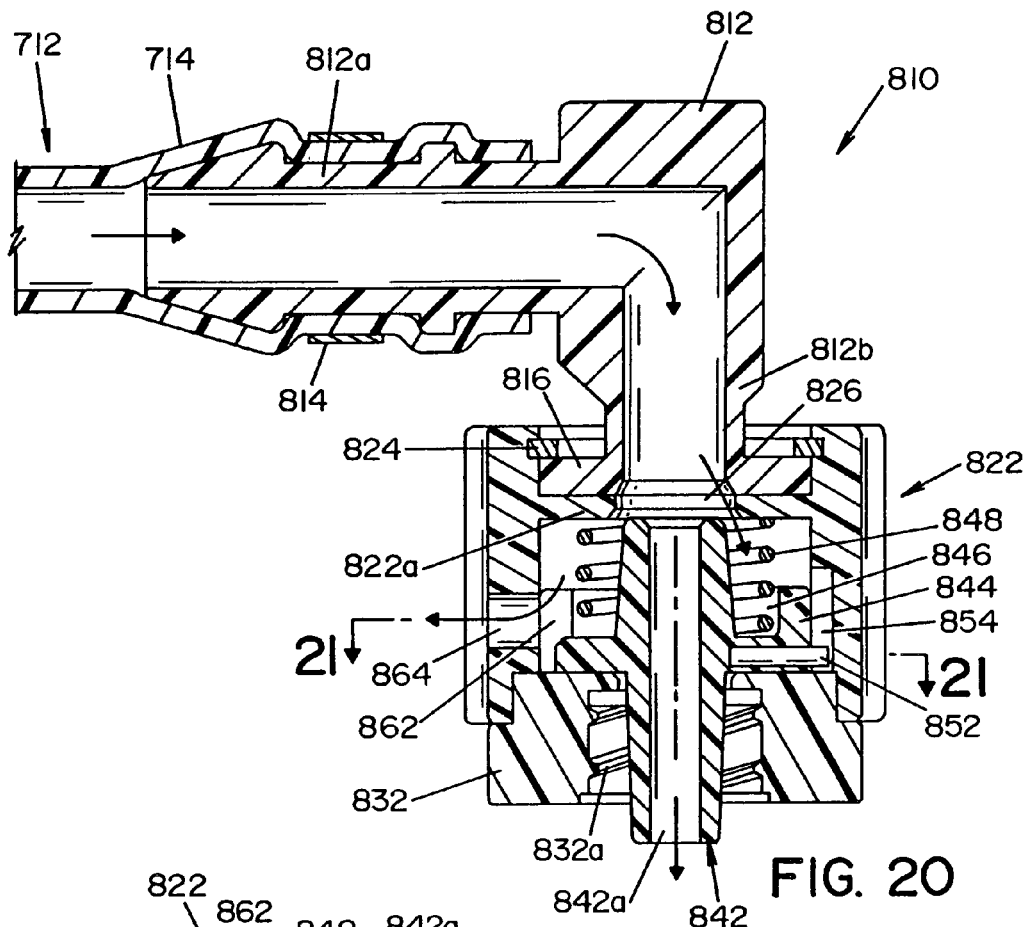
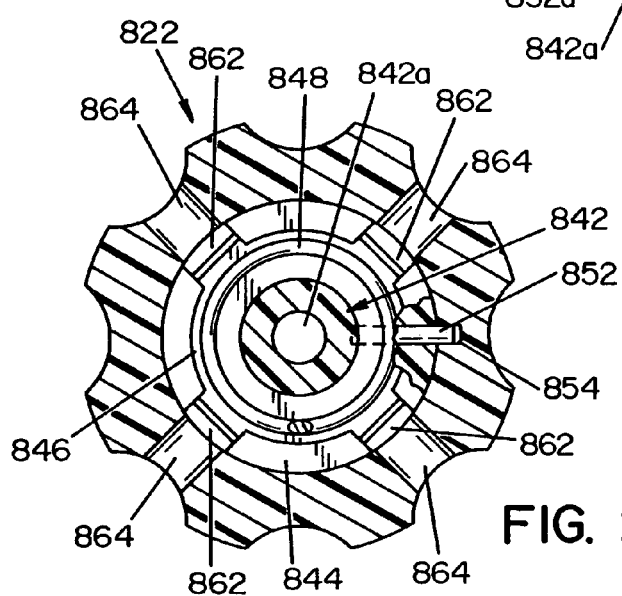

METHOD AND DEVICE FOR DEACTIVATING ITEMS AND FOR MAINTAINING SUCH ITEMS IN A DEACTIVATED STATE

FIELD OF THE INVENTION

The present invention relates to disinfection or deactivation of medical, dental, pharmaceutical, veterinary or mortuary instruments and devices, and more particularly to a method and apparatus for deactivating items and for maintaining the items in a deactivated state.

BACKGROUND OF THE INVENTION

Medical, dental, pharmaceutical, veterinary or mortuary instruments and devices that are exposed to blood or other body fluids require thorough cleaning and anti-microbial deactivation between each use. Liquid microbial deactivation systems are now widely used to clean and deactivate instruments and devices that cannot withstand the high temperatures of a steam deactivation system. Liquid microbial deactivation systems typically operate by exposing the medical devices and/or instruments to a liquid disinfectant or deactivation composition, such as peracetic acid or some other strong oxidant.

In such systems, the instruments or devices to be cleaned are typically placed within a deactivation chamber within the liquid microbial deactivation system, or in a container that is placed within the deactivation chamber. During a deactivation cycle, a liquid disinfectant is then circulated through a liquid circulation system that includes the deactivation chamber (and the container therein).

Following a deactivation cycle in a conventional reprocessor, the deactivated items are manually removed from the reprocessor, or from a tray or container that holds the items in the reprocessor during the deactivation cycle. The deactivated items are typically transferred to a storage cassette, or are sealed in a protective anti-microbial wrap to prevent deactivation of the items once they (the items) have been removed from the reprocessor. However, no matter how carefully the items are removed from the reprocessor, the items are exposed to airborne bio-contaminants once the items are exposed to the surrounding atmosphere. Thus, if the items are stored for a prolonged period of time before their next use in an operating room or the like, the bio-contaminants have time to populate within the storage cassette or anti-microbial wrap.

The present invention overcomes these and other problems and provides a method and apparatus for deactivating items, and a device for storing such deactivated items.

SUMMARY OF THE INVENTION

In accordance with a preferred embodiment of the present invention, there is provided a container for holding items to be microbially deactivated in a reprocessor. The container is comprised of a generally cup-shaped tray having a bottom wall and a continuous side wall extending to one side from the periphery of the bottom wall. The side wall has a free edge, and the bottom wall and the side wall define a cavity for receiving instruments and items to be microbially deactivated. A rigid first seal element is formed along the free edge of the side wall. A lid is attachable to the tray. The lid has a rigid second seal element thereon. The second seal element is dimensioned to matingly engage the first seal element on the tray, wherein a convoluted path is defined between the first seal element and the second seal element.

In accordance with another aspect of the present invention, there is provided a container for holding items to be microbially deactivated in a reprocessor. The container includes a tray for holding the items to be deactivated, and a lid that is operable to cover the tray. The lid and the tray define a cavity to hold the items to be deactivated. Interacting seal means on the tray and the lid form a seal between the tray and the lid. The seal means defines a convoluted path between the cavity and the of the container.

In accordance with another aspect of the present invention, there is provided a reprocessor for microbially deactivating items. The reprocessor has a circulation system for circulating a microbial deactivation fluid through a deactivation chamber that forms part of the circulation system. A container is provided for insertion into the deactivation chamber for holding items to be microbially deactivated. The container includes a tray and a lid. The tray and lid have interlocking, integrally formed, rigid seal elements formed thereon to form a seal between the tray and the lid.

One advantage of the present invention is the provision of an apparatus for deactivating medical instruments and items.

Another advantage of the present invention is the provision of a container for holding medical instruments and items during a microbial deactivation process, which container maintains the instruments in a deactivated environment therein for a prolonged period of time after removal of the container from the apparatus.

A still further advantage of the present invention is a container as described above that may be used as a storage device for storing the microbially deactivated instruments until use.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 20 is a sectional view showing a connector assembly for connecting the lumen flush tubes to a fitting on the instrument showing an internal valve arrangement on the fitting;

FIG. 21 is a sectional view taken along lines 21—21 of FIG. 20;

DETAILED DESCRIPTION OF PREFERRED EMBODIMENT

Figure 1:
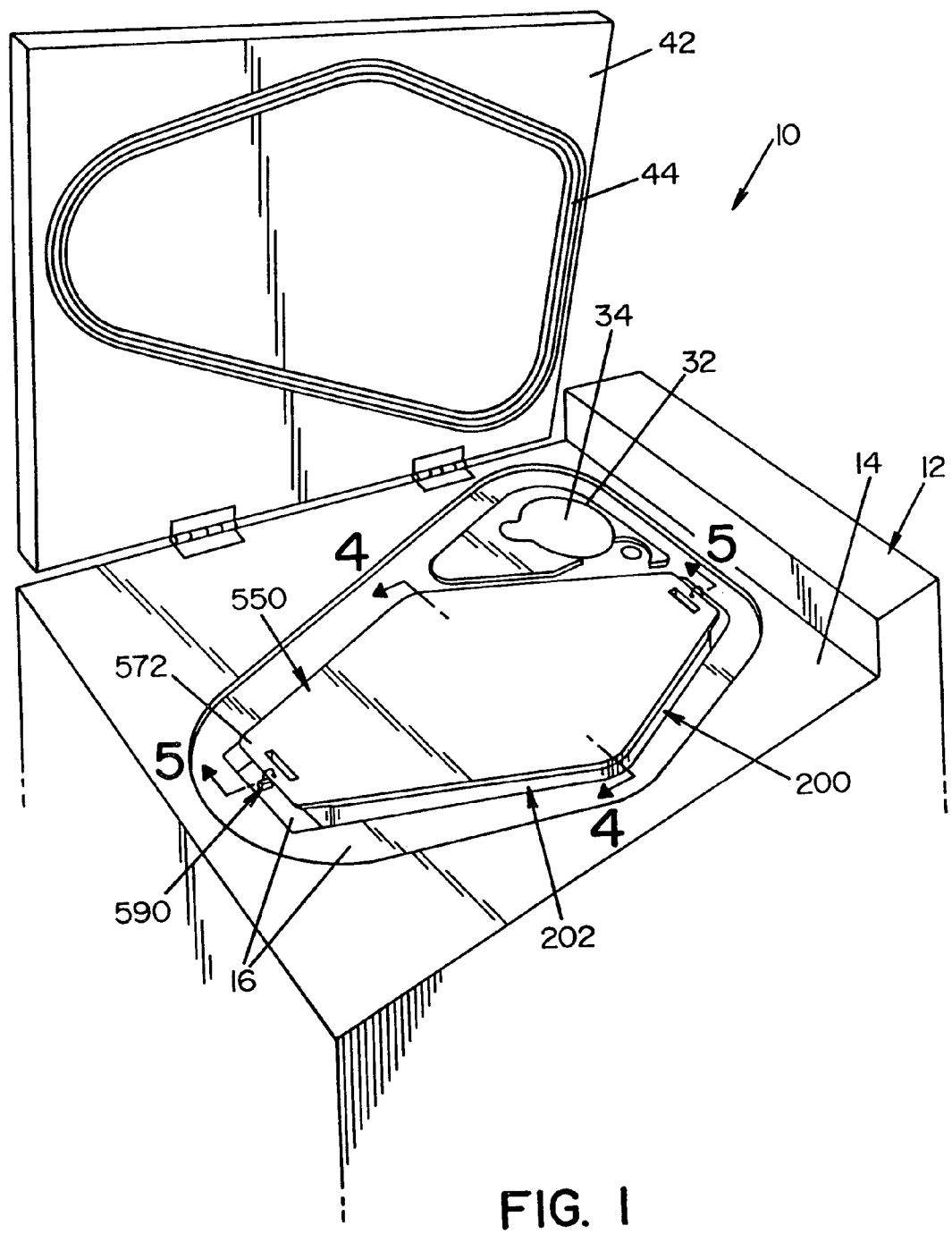
FIG. 1 is a perspective view of an upper portion of an automated reprocessor for microbially deactivating instruments and devices, according to the present invention.

Referring now to the drawings wherein the showings are for the purpose of illustrating a preferred embodiment of the invention only, and not for the purpose of limiting same, FIG. 1 shows an upper portion of an apparatus 10 for microbially deactivating medical instruments and other devices, illustrating a preferred embodiment of the present invention.

Apparatus 10 includes a housing structure 12 having an upper panel 14 that defines a recess or cavity 16. Cavity 16 is dimensioned to receive a container 200. Container 200 is provided to receive the devices or instruments to be deactivated. Container 200 is dimensioned to be received within recess or cavity 16, as illustrated in FIG. 1. A well 32 (schematically illustrated in FIG. 2) is formed adjacent cavity 16. Well 32 is dimensioned to receive a chemical delivery container 34 that contains dry chemical reagents that, when combined with water, form the microbial deactivation fluid used in apparatus 10.

A manually operable lid 42 is movable between an opened position (shown in FIG. 1) allowing access to cavity 16, and a closed position (shown in FIG. 2) closing or covering cavity 16. A seal element 44 surrounds cavity 16 and forms a fluid-tight seal between lid 42 and panel 14 when lid 42 is in a closed position. Latch means (not shown) are provided for latching and securing lid 42 in a closed position during a deactivation cycle. Cavity 16 essentially defines a deactivation chamber 50 when lid 42 is in a closed position.

Figure 2:
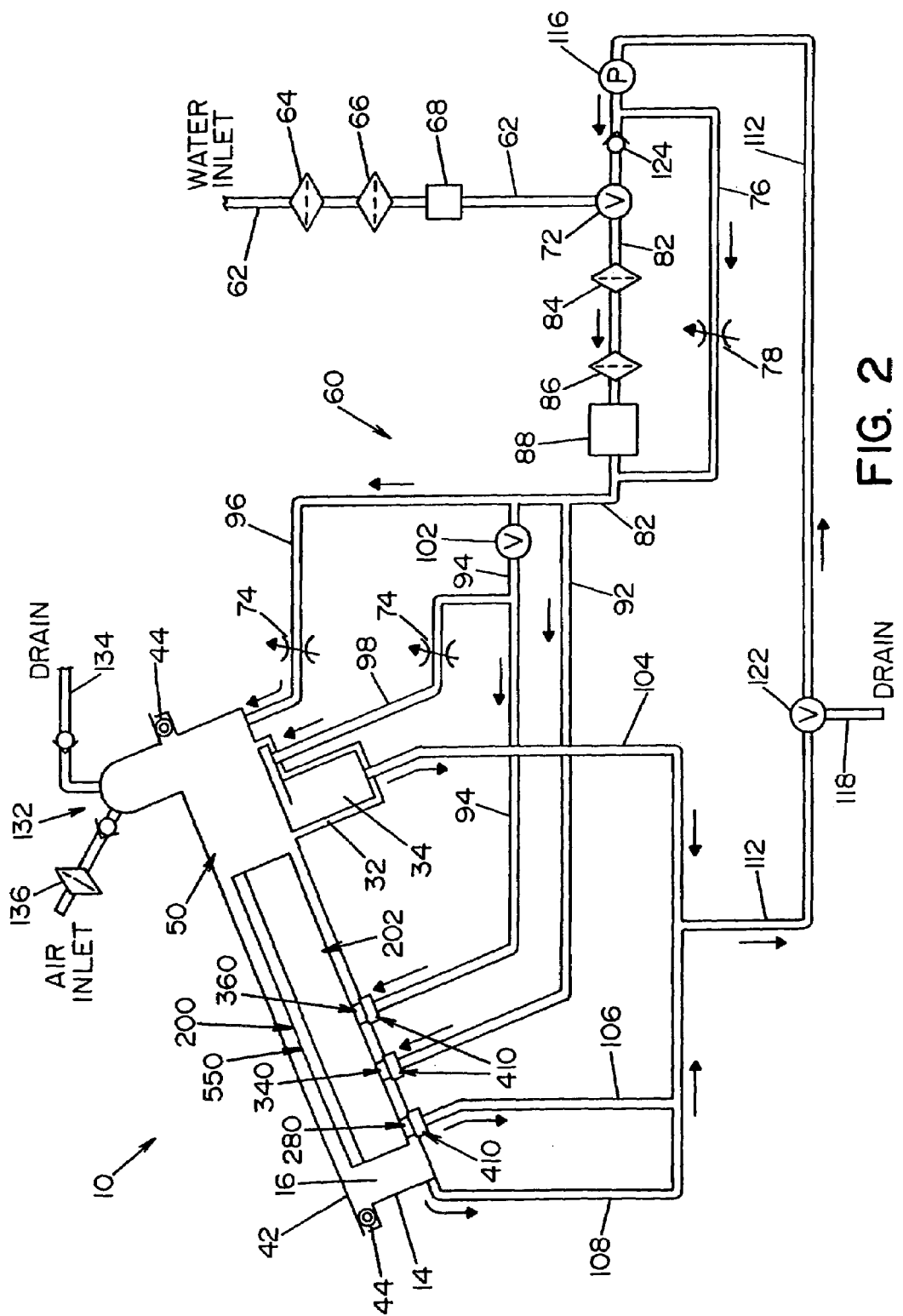
FIG. 2 is a schematic-diagram of the reprocessor shown in FIG. 1.

FIG. 2 shows a simplified, schematic piping diagram of apparatus 10. A fluid circulation system 60 provides the microbial deactivation fluid to deactivation chamber 50 and is further operable to circulate the microbial deactivation fluid through deactivation chamber 50 and container 200. Fluid circulation system 60 includes a water inlet line 62 that is connected to a source of heated water (not shown). A pair of macro filters 64, 66 are provided in water inlet line 62 to filter large contaminants that may exist in the incoming water. An ultraviolet (UV) treatment device 68 for deactivating organisms within the water source is preferably provided in inlet line 62. A water valve 72 controls the flow of water from water inlet line 62 to a system feeder line 82. System feeder line 82 includes two filter elements 84, 86 in series to filter microscopic organisms from the incoming water so as to provide sterile water to fluid circulation system 60. A heating element 88 is disposed in system feeder line 82 downstream from filter elements 84, 86. System feeder line 82 splits into a first branch feeder line 92 and a second branch feeder line 94. First and second branch feeder lines 92, 94 communicate with container 200 within deactivation chamber 50. First and second branch feeder lines 92, 94 are connected to container 200 through fluid inlet assemblies 340, 360, schematically illustrated in FIG. 2. Fluid inlet assemblies 340, 360 are adapted to operatively interact with valve actuating connectors 410, mounted to panel 14, as shall be described in greater detail below. A third branch feeder line 96 is connected to deactivation chamber 50 itself.

A supplemental branch feeder line 98 splits off of second branch feeder line 94 and is directed to an inlet portion of chemical delivery container 34 that contains dry chemical reagents that form the microbial deactivation fluid used in apparatus 10. A valve 102 controls the flow through supplemental branch feeder line 98 to chemical dispensing container 34 and through line 94 connected to container 200. Flow restrictors 74 are provided in third branch feeder line 96 and supplemental branch feeder line 98 to limit flow therethrough. Chemical dispensing container 34 is disposed within well 32 formed within panel 14 of housing structure 12.

A branch return line 104 extends from chemical delivery container 34 and is connected to system return line 112. Likewise, branch fluid return lines 106, 108 extend from container 200 and deactivation chamber 50, respectively, and are connected to system return line 112. A fluid outlet assembly 280 on container 200 connects with branch return line 106 via a valve actuating connector 410 on panel 14, as shall be described in greater detail below.

System return line 112 connects back with water inlet line 62 and fluid feeder line 82, as illustrated in FIG. 2. A pump 116 is disposed within system return line 112. Pump 116 is operable to circulate fluid, i.e., water and the microbial deactivation fluid, through fluid circulation system 60. A drain line 118 is connected to system return line 112. A drain valve 122 controls fluid flow through drain line 118. A directional check valve 124 is disposed in system feeder line 82 between water inlet line 62 and pump 116. A filter bypass line 76 communicates with fluid system feeder line 82 on opposite sides of filters 84, 86. Specifically, one end of bypass line 76 is connected to system feeder line 82 between pump 116 and directional check valve 124. The other end of bypass line 76 communicates with system feeder line 82 beyond filters 84, 86 and heating device 88, but before where first, second and third branch feeder lines 92, 94 and 96 are formed. A flow restrictor 78 is provided in filter bypass line 76 to limit flow therethrough.

A system microprocessor or microcontroller (not shown) controls the operation of the circulation system, as shall be described in greater detail below. The operation of the circulation system includes a fill phase, a circulation phase and a drain phase, as shall also be described in greater detail below. To facilitate operation of the fill phase, circulation phase and drain phase, an air inlet/fluid overflow assembly 132 is provided at the uppermost portion of deactivation chamber 50 in fluid communication therewith. Air inlet/fluid overflow assembly 132 includes an overflow drain 134 to allow excess fluid within deactivation chamber 50 and circulation system 60 to overflow into a drain, and an air inlet to provide air into deactivation chamber 50 to facilitate draining thereof. A filter 136 is provided in the air inlet to filter the incoming air.

Referring now to FIGS. 3–7, container 200 is best seen. Container 200 is generally comprised of a tray 202 and a lid 550 that is attachable thereto. Tray 202 is generally cup-shaped and has a bottom wall 204 and a continuous side wall 206 that extends about the periphery of bottom wall 204, and that extends to one side thereof. Bottom wall 204 and side wall 206 define a cavity 208 in which instruments or other items to be deactivated are to be inserted. In the embodiment shown, tray 202 is generally oval in shape, although other shapes are contemplated within the scope of the present invention.

Figure 8:
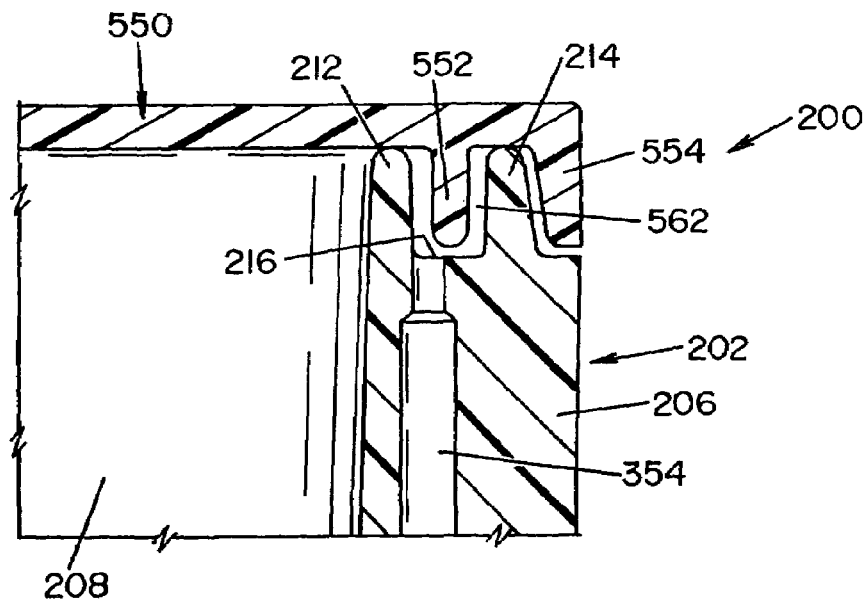
FIG. 8 is an enlarged view of the identified area shown in FIG. 4.
Figure 9:
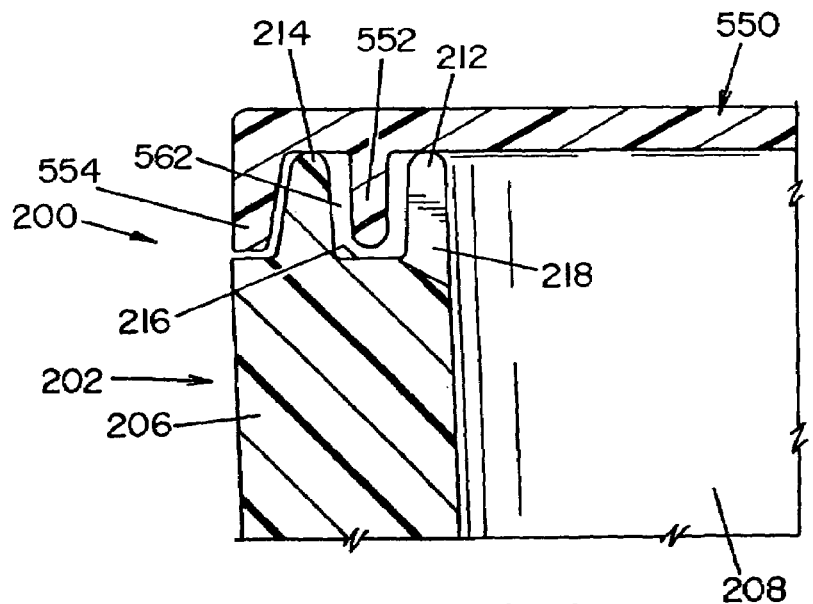
FIG. 9 is an enlarged view of the identified area shown in FIG. 4.

The upper edge of side wall 206, best seen in FIGS. 8 and 9, is shaped to define a portion of a seal element. In the embodiment shown, the upper edge of side wall 206 is formed to have two, spaced-apart rails 212, 214 that extend continuously along the upper edge of side wall 206. Rails 212, 214 define a channel 216, best seen in FIG. 11 that likewise extends continuously about the upper edge of side wall 206. Rails 212, 214 on tray 202 are dimensioned to operatively engage corresponding elements on lid 550, as shall be described in greater detail below.

The bottom wall has an upper surface, designated 204a in the drawings. Two spaced-apart, generally concave mounting pads 222, 224 extend from upper surface 204a of bottom wall 204. Each mounting pad 222, 224 includes an arcuate-shaped slot or recess 226 formed therein. Mounting pad 222 has a recess or relief 232 formed therein. A pair of spaced-apart connector fittings 234, 236 is mounted within recess or relief 232 of mounting pad 222. Upper surface 204a of bottom wall 204 is generally contoured and includes a plurality of recesses 242, 244, 246 and 248 that are dimensioned to receive and support portions of the instruments or items to be microbially deactivated so as to facilitate positioning such instruments or items within cavity 208 of tray 202. Two recesses 252, 254 are formed between mounting pads 222, 224 at the ends thereof. Recesses 252, 254 include directional spray nozzles 256, 258.

In the embodiment shown, three fluid assemblies 280, 340, 360, two inlet fluid assemblies 340, 360 and one fluid outlet assembly 280, are formed in tray 202 to allow a microbial deactivation fluid to flow into, through and out of container 200. Basically, first fluid inlet assembly 340 facilitates flow of a microbial deactivation fluid into tray 202 through nozzles 256, 258 and to the upper edge of side wall 206, as shall be described in greater detail below.

Second fluid inlet assembly 360 facilitates fluid flow to connector fittings 234, 236 within recess 232 in mounting pad 222. Connector fittings 234, 236 in turn are connectable to certain medical devices and instruments by flexible connectors 712 (best seen in FIGS. 18 and 19) to direct the microbial deactivation fluid through lumens and passages in such instruments.

Outlet fluid assembly 280 is provided to allow fluid to be drained from container 200.

Figure 7:
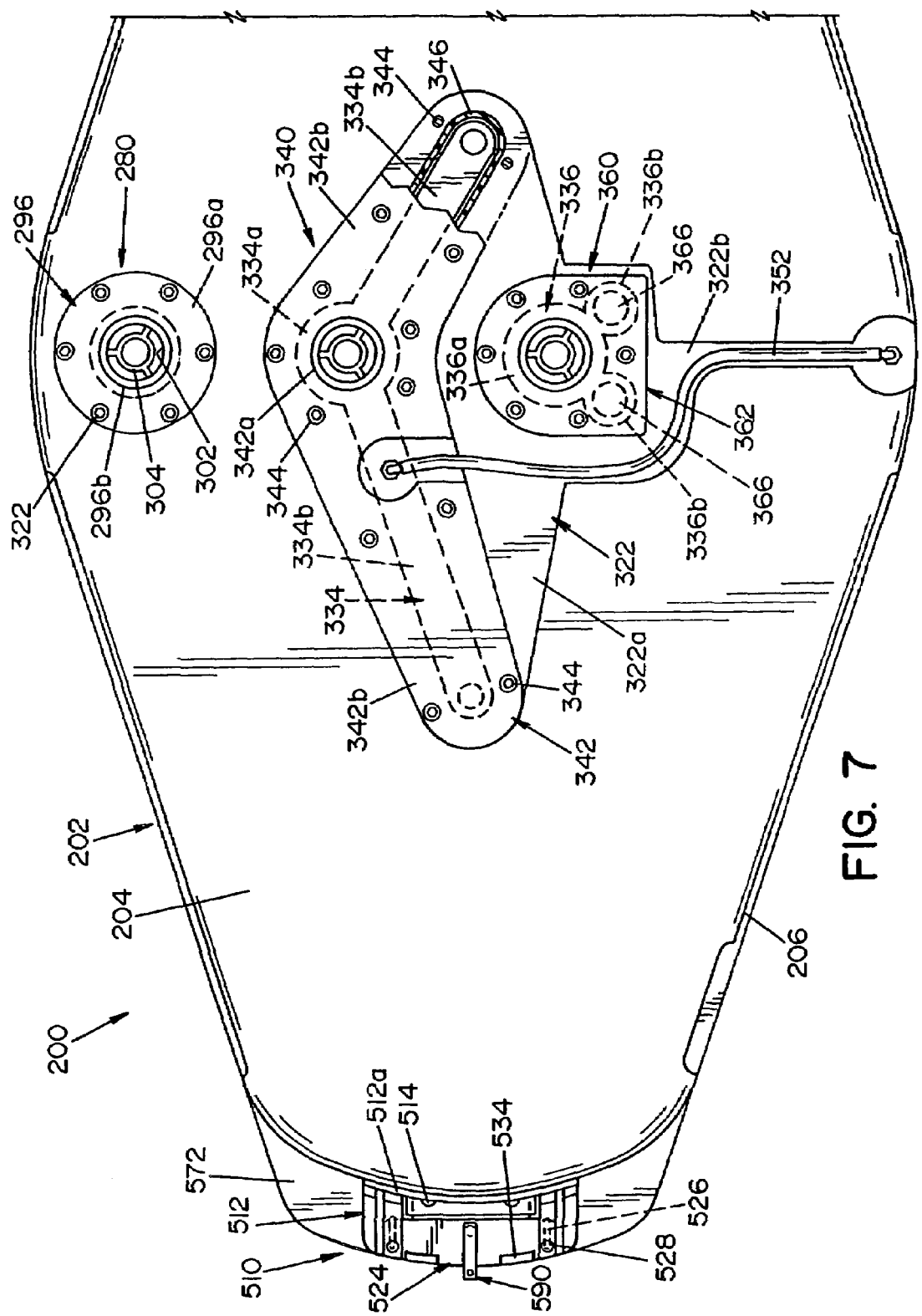
FIG. 7 is an enlarged, bottom plan view of a portion of the container.

Each of the aforementioned fluid assemblies 280, 340, 360 is comprised of many like elements. A general understanding of three fluid assemblies can be realized with reference to FIG. 12, wherein fluid outlet assembly 280 on tray 202 is best seen. A drain opening 292 is formed in bottom wall 204 of tray 202 near side wall 206. Drain opening 292 is preferably located at what will be the lowest point in container 200 when container 200 is within deactivation chamber 50. An enlarged counter-sunk opening 294 is formed in the bottom surface of bottom wall 204 to receive a mounting plate 296. Mounting plate 296 is cylindrical in shape and has a cylindrical body portion 296a dimensioned to fit within counter-sunk opening 294 in tray 202. A cylindrical, tubular sleeve 296b extends downwardly from mounting plate 296. Sleeve 296b defines a cylindrical opening 302 that extends into a generally cup-shaped cavity formed in body portion 296a of mounting plate 296. An open grill or lattice-like structure 304 is disposed within cylindrical opening 302 defined by tubular sleeve 296b, as best seen in FIG. 7. A flexible valve element 312 is mounted to tray 202 by mounting plate 296.

Figure 12:
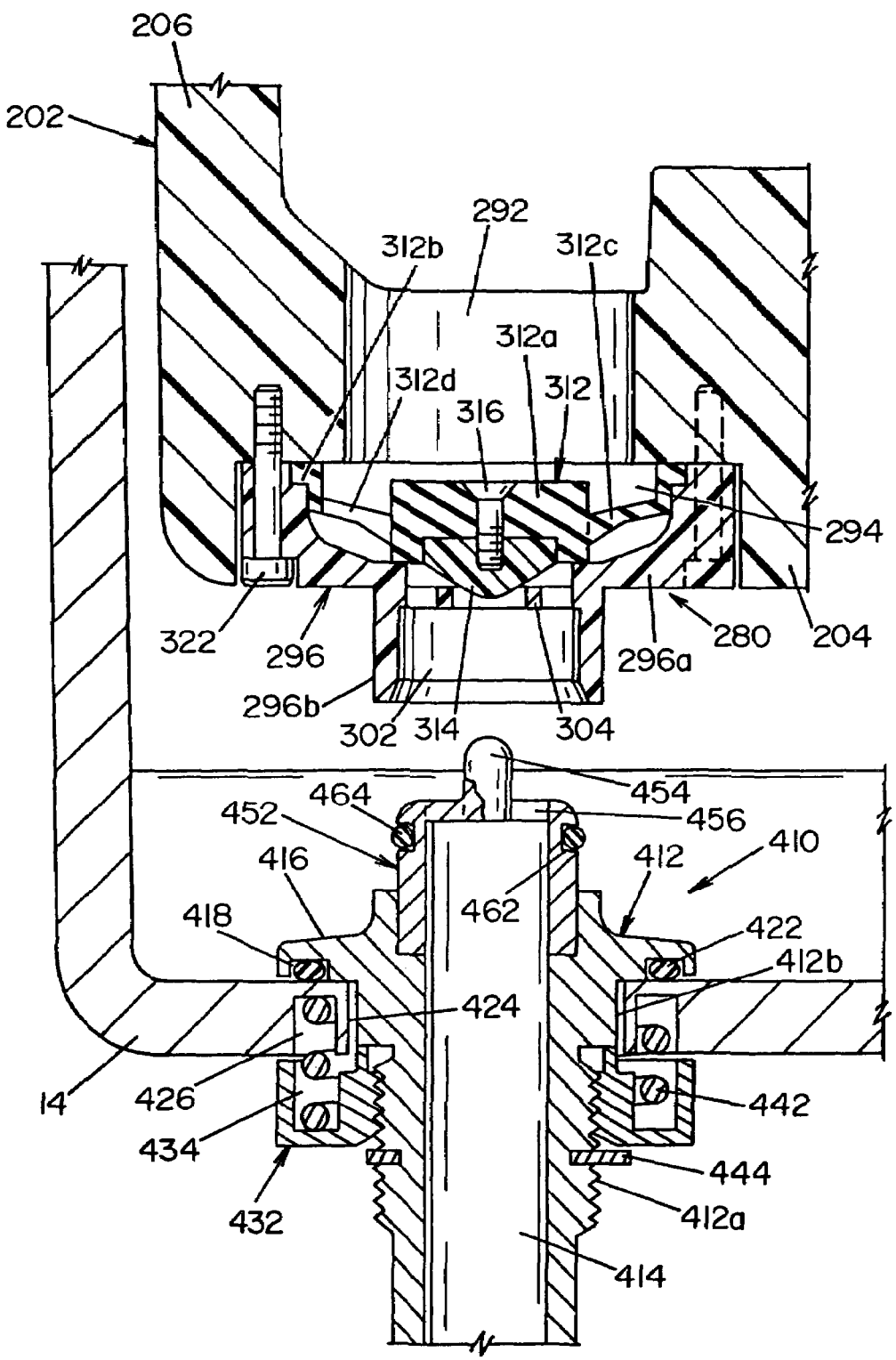
FIG. 12 is an enlarged view showing an outlet valve of the container spaced-apart from a male outlet connector on the reprocessor housing.

Valve element 312 includes a cylindrical central body portion 312a that is connected to an outer, annular, flanged ring portion 312b by a plurality of radially extending arm portions 312c that define opening 312d. Valve element 312 is preferably formed of a resilient, flexible polymeric material and is preferably molded as an integral piece. A cylindrical recess is formed in the bottom of central body portion 312a to receive a rounded or domed cap element 314 formed of a hard, tough, durable polymeric material. Cap 314 is secured to central body portion 312a of valve element 312 by a conventional fastener 316, as illustrated in FIG. 12. Flanged ring portion 312b of valve element 312 is dimensioned to be captured by a recess in mounting plate 296. Mounting plate 296 is attached to tray 202 within counter-sunk opening 294 by conventional fasteners 322.

Figure 13:
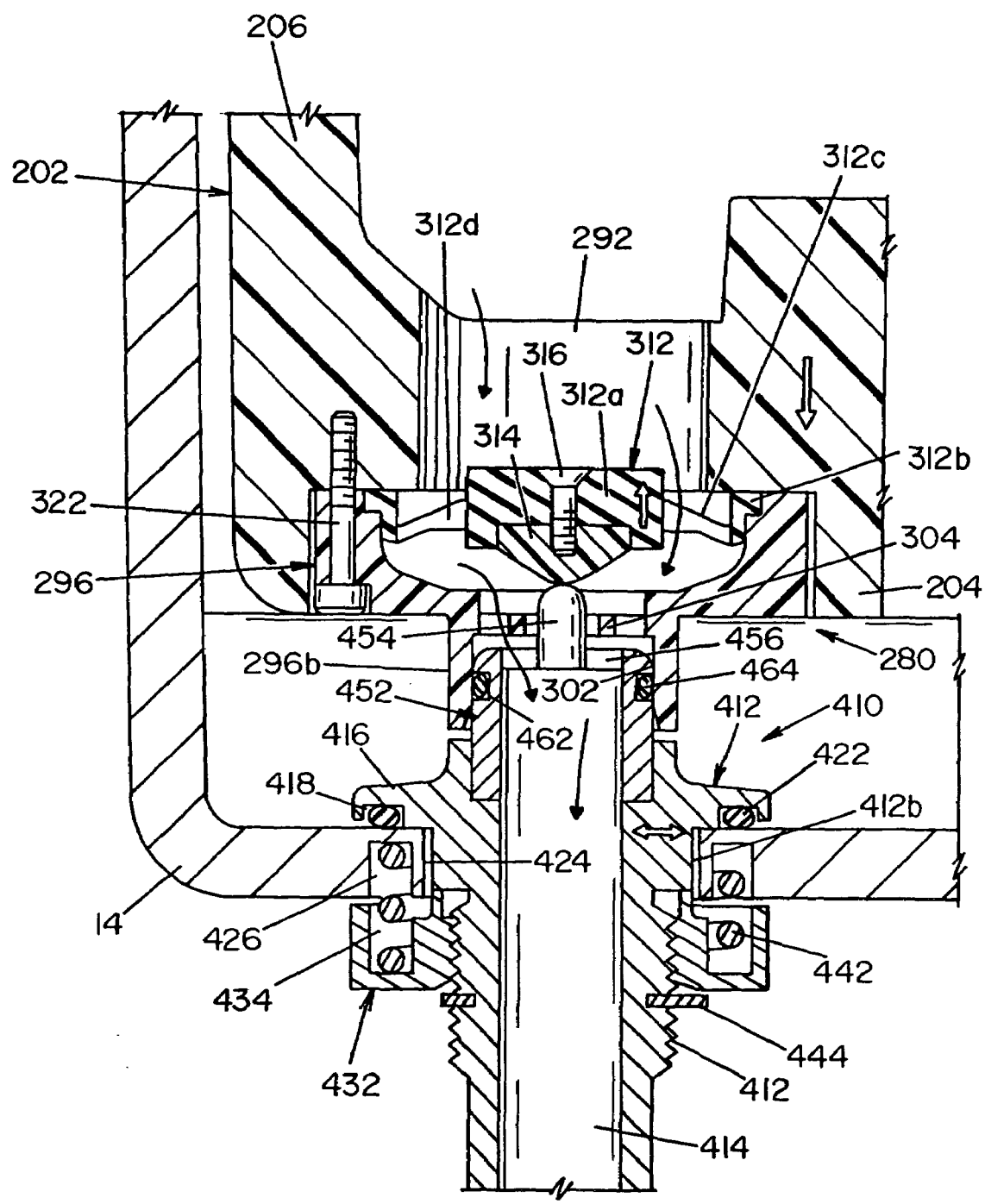
FIG. 13 is an enlarged, sectional view showing the outlet valve of the container in operative engagement with the male connector on the reprocessor housing.

Valve element 312 is molded or otherwise formed to assume a first, normal position, as shown in FIG. 12, wherein central body portion 312a of valve element 312 engages or "seats" itself against the inner edge of mounting plate 296 that surrounds cylindrical bore 302, thereby effectively closing the opening through bottom wall 204 of tray 202. Valve element 312 is moveable to a second position, as best seen in FIG. 13, wherein central body portion 312a of valve element 312 is moved away from mounting plate 296 to an opened position, and wherein a continuous fluid passage is formed through drain opening 292, through openings 312d between arms 312c of valve element 312 and through sleeve portion 296b of mounting plate 296.

Figure 5:
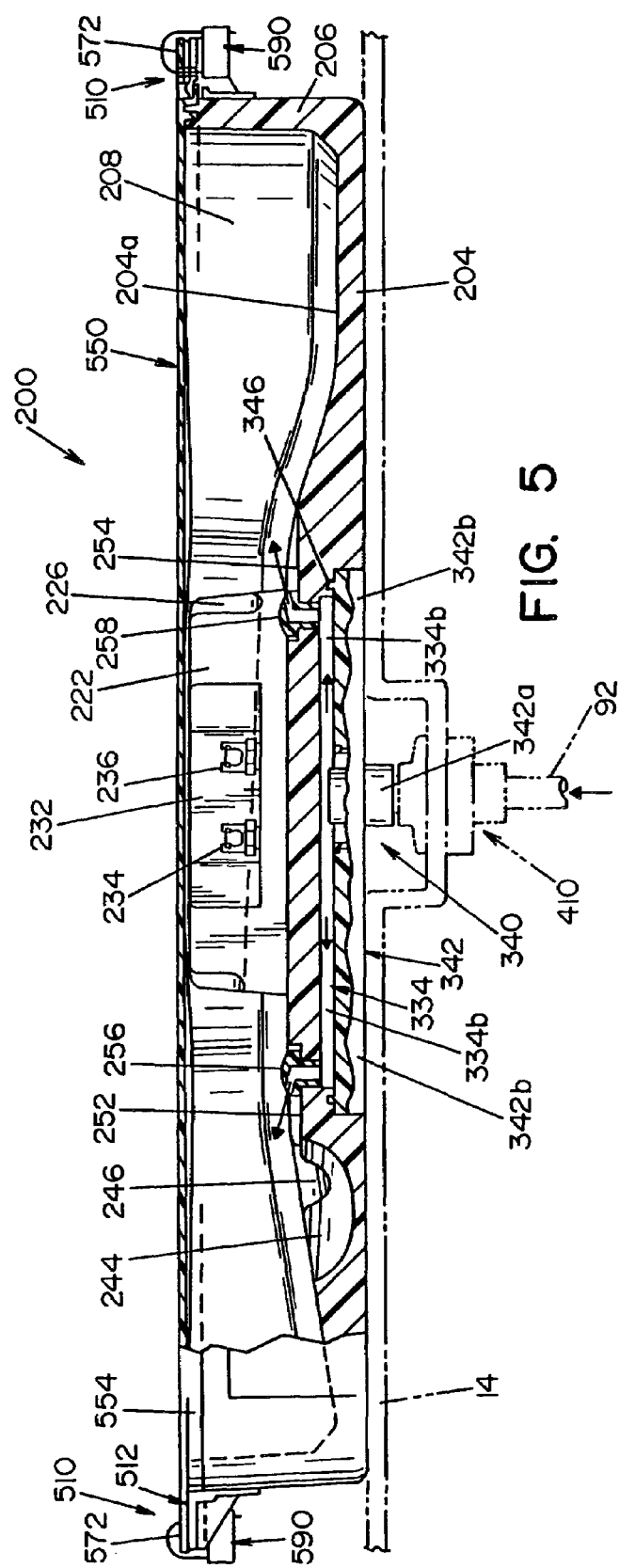
FIG. 5 is a sectional view taken along lines 5—5 of FIG. 1.
Figure 6:
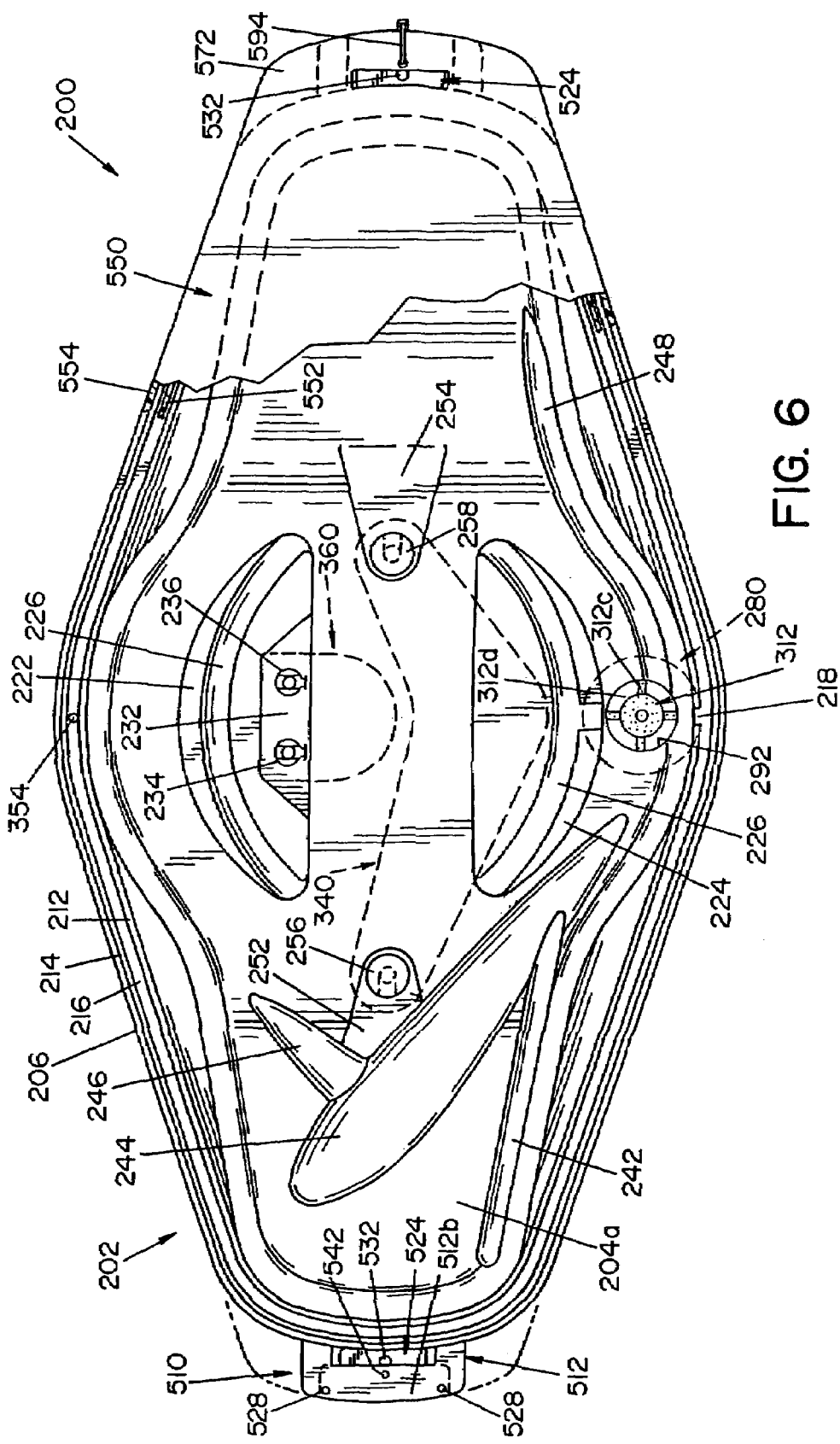
FIG. 6 is a top plan view of the container, showing a portion of a lid broken away.

Referring now to FIGS. 5 and 7, first and second fluid inlet assemblies 340, 360 are best seen. In the embodiment shown, fluid inlet assemblies 340, 360 are disposed within a relatively large cavity or depression 322 formed in the bottom wall of tray 202. Cavity 322 includes a large area 322a that is generally centrally located on the bottom surface of tray 202 and a portion 322b that extends to one side of tray 202. The bottom of cavity 322 is defined by a generally planar surface. First and second passage-defining cavities 334, 336 (best seen in phantom in FIG. 7) are formed in the planar surface that defines recess 322. First passage-defining cavity 334 is generally V-shaped, and has a circular portion 334a and two outwardly extending arm portions 334b. Arm portions 334b of first passage-defining cavity 334 communicate with nozzles 256, 258 on the opposite side of bottom wall 204, as best seen in FIG. 5.

Second passage-defining cavity 336 has a large, circular portion 336a that communicates with two, smaller circular portions 336b that are tangent thereto. Two smaller circular portions 336b of second passage-defining cavity 336 communicate with connector fittings 234, 236 that are disposed within recess or relief 232 in mounting pad 222 on the opposite side of bottom wall 204.

Figure 3:
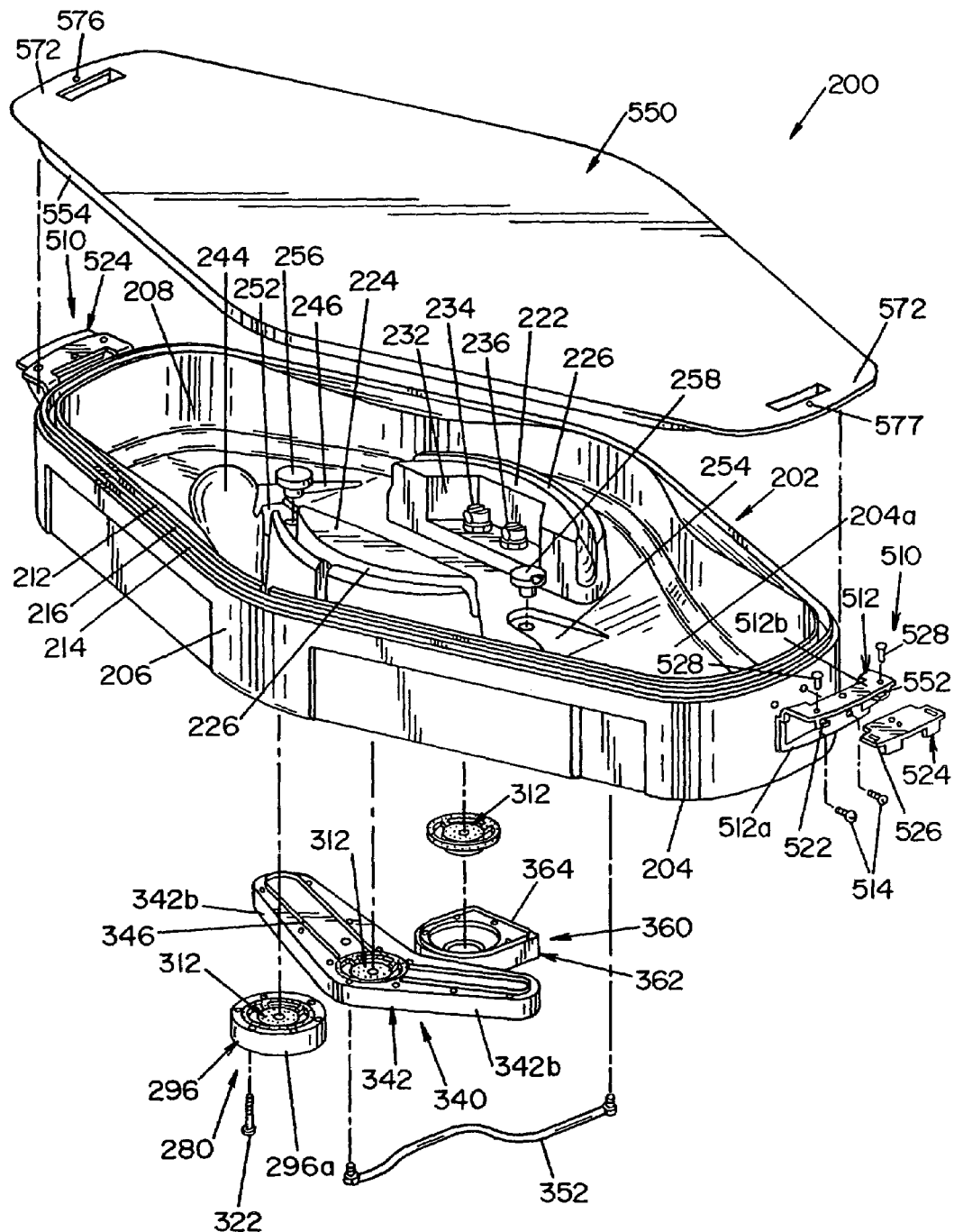
FIG. 3 is an exploded view of a container for holding items to be microbially deactivated in the reprocessor shown in FIG. 1.

A mounting plate 342, best seen in FIG. 3, is dimensioned to be attached to bottom wall 204 of tray 202 and cover first passage-defining cavity 334. In this respect, mounting plate 342 is generally V-shaped and has elongated arms 342b to cover arm portions 334b of first passage-defining cavity 334. Mounting plate 342 is generally flat, with a downwardly extending sleeve 342a (best seen in FIGS. 4 and 5). Mounting plate 342 is dimensioned to capture and mount valve element 312 of the type heretofore described. In this respect, mounting plate 342 is attached to tray 202 within recess 322 by a plurality of conventional fasteners 344. A sleeve 342a extends from mounting plate 342, and defines an opening that communicates with valve element 312 that is disposed between mounting plate 342 and tray 202. Mounting plate 342 covers the open side of first passage-defining cavity 334, and thus defines a fluid passage (best seen in FIG. 5) that connects valve element 312 (that is captured by mounting plate 342) to spray nozzles 254, 256 on the other side of bottom wall 204. In the embodiment shown, an elongated U-shaped rail or key 346 is formed on the upper surfaces of each leg portion 342b of mounting plate 342 to locate and lock mounting plate 342 in mating grooves formed within recess 322 of tray 202. As best seen in FIG. 7, a tube or hose 352 is attached at one end to mounting plate 342 to communicate with the fluid passage defined by mounting plate 342 and fluid-defining cavity 334 within tray 202. The other end of tube or hose 352 is connected to a channel 354 (best seen in FIGS. 4 and 8) that communicates with channel 216 along the upper edge of side wall 206.

Referring now to FIG. 3, second fluid inlet assembly 360 is best seen. Like first fluid inlet assembly 340, second fluid inlet assembly 360 includes mounting plate 362, that is dimensioned to capture and hold valve element 312 of the type heretofore described. Mounting plate 362 of second fluid inlet assembly 360 is attached within extension portion 322b of recess 322 by conventional fasteners. Mounting plate 362 is positioned to be in registry with, and to cover, second-passage defining cavity 336 within recess 322. Like mounting plate 342 in first inlet assembly 340, mounting plate 362 of second fluid inlet assembly 360 includes a key or rail 364 that extends about the periphery of mounting plate 362 to locate and lock mounting plate 362 into position in recess 322 in bottom wall 204 of tray 202. Mounting plate 362 essentially covers second-passage defining cavity 336 to define a fluid passage between valve element 312 that is held by mounting plate 362 and openings 366 that are connected to connector fittings 234, 236 on the opposite side of bottom wall 204.

In summary, outlet fluid assembly 280, and first and second inlet fluid assemblies 340, 360 each include like valve elements 312 that are operatively mounted to the bottom of tray 202. Valve element 312 of outlet fluid assembly 280 communicates with branch return line 106. Valve element 312 of first fluid inlet assembly 340 connects branch feeder line 92 with spray nozzles 256, 258 within cavity 208 of tray 202 and with the upper edge of side wall 206. Valve element 312 of second fluid inlet assembly 360 connects with connector fittings 234, 236 on mounting pad 222 within cavity 208 of tray 202. All of the valve elements 312 have a normally closed position that prevents flow of fluid therethrough. As indicated above, valve elements 312 of the aforementioned fluid assemblies 280, 340, 360 are dimensioned to operatively interact with a valve actuating connector 410 on panel 14 of apparatus housing 12. In a preferred embodiment of the present invention, valve actuating connectors 410 for fluid assemblies 280, 340, 360 are identical. Accordingly, only one valve actuating connector 410 shall be described in detail, it being understood that such description applies equally to the other valve actuating connector 410.

Referring now to FIGS. 12 and 13, valve actuating connector 410 associated with outlet fluid assembly 280 is best seen. In accordance with one aspect of the present invention, valve actuating connector 410 is mounted to panel 14 of housing 12 of apparatus 10 to enable actuating connector 410 to "float," i.e., move relative to panel 14. In the embodiment shown, valve actuating connector 410 has a cylindrical, tubular connector body 412 defining a fluid passage 414 therethrough. Connector body 412 has an outwardly extending, annular flange 416 formed at the free end thereof. Flange 416 has a downwardly facing annular groove 418 dimensioned to receive an O-ring 422. Connector body 412 includes a threaded portion 412a. Between flange 416 and threaded portion 412a is a cylindrical body portion 412b dimensioned to be received within a circular opening 424 within panel 14. The diameter of opening 424 in panel 14 is larger than the diameter of cylindrical body portion 412b of connector body 412. An annular groove 426 is formed around opening 424 in panel 14. A threaded collar 432 is provided to secure connector body 412 to panel 14, as illustrated in FIGS. 12 and 13. Collar 432 includes an annular groove 434 formed therein. Groove 434 in collar 432 is dimensioned to match annular groove 426 within panel 14. A biasing element 442, in the form of a helical spring, is disposed within annular grooves 426, 434 formed within panel 14 and threaded collar 432. Threaded collar 432 is maintained in position on connector body 412 by a retaining ring 444 disposed within an annular slot formed within connector body 412. The biasing effect of helical spring 442 causes flange 416 of tubular connector body 412 to force O-ring 422 into engagement with the upper surface of panel 14. Valve actuating connector 410 is thus free to move a limited amount within cylindrical opening 424 in panel 14. Opening 424 is at all times sealed by O-ring 422 that is forced into engagement with panel 14 by the biasing effect of helical spring 442.

Cap 452 is inserted into a counter-bored opening formed in the free, upper end of connector body 412. Cap 452 is cylindrical in shape and includes an axially extending pin 454 at the end thereof. Openings 456 are formed through the end of cap 452 to communicate with fluid passage 414 defined by tubular connector body 412. An annular groove 462 is formed within cap 452 to receive O-ring 464. Cap 452 is dimensioned to be received within opening 302 defined by sleeves on the respective fluid assemblies 280, 340, 360 wherein O-ring 464 sealingly engages inner surface 302 of such sleeve. The lower end of connector body 412, shown in FIGS. 12 and 13, is connected to, or forms part of, branch return line 106 of fluid circulation system 60, as illustrated in FIG. 2. In this respect, two other valve actuating connectors 410 are attached to panel 14 to operatively engage first and second fluid inlet assemblies 340, 360, as seen in FIG. 2. Connector body 412 of valve actuating connector 410 that is associated with first fluid inlet assembly 340 is connected to, or forms part of, first branch feeder line 92. Connector body 412 of valve actuating connector 410 that is associated with second fluid inlet assembly 360, is connected to, or forms part of, second branch feeder line 94.

Figure 10:
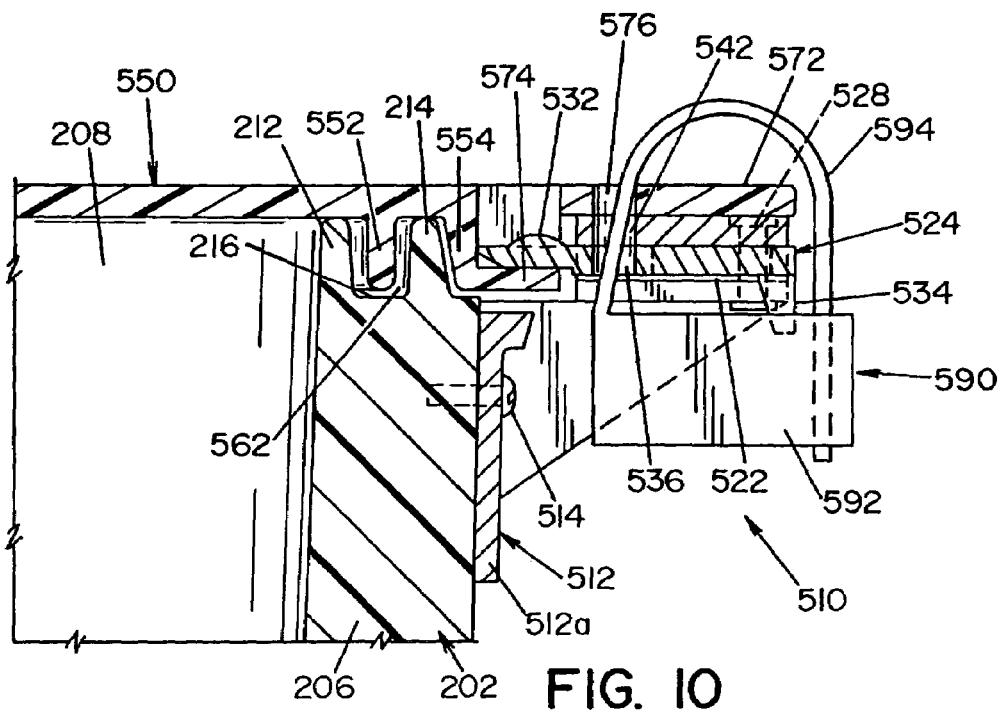
FIG. 10 is an enlarged view of a portion of the lid and container, showing a locking arrangement in a locked configuration.
Figure 11:
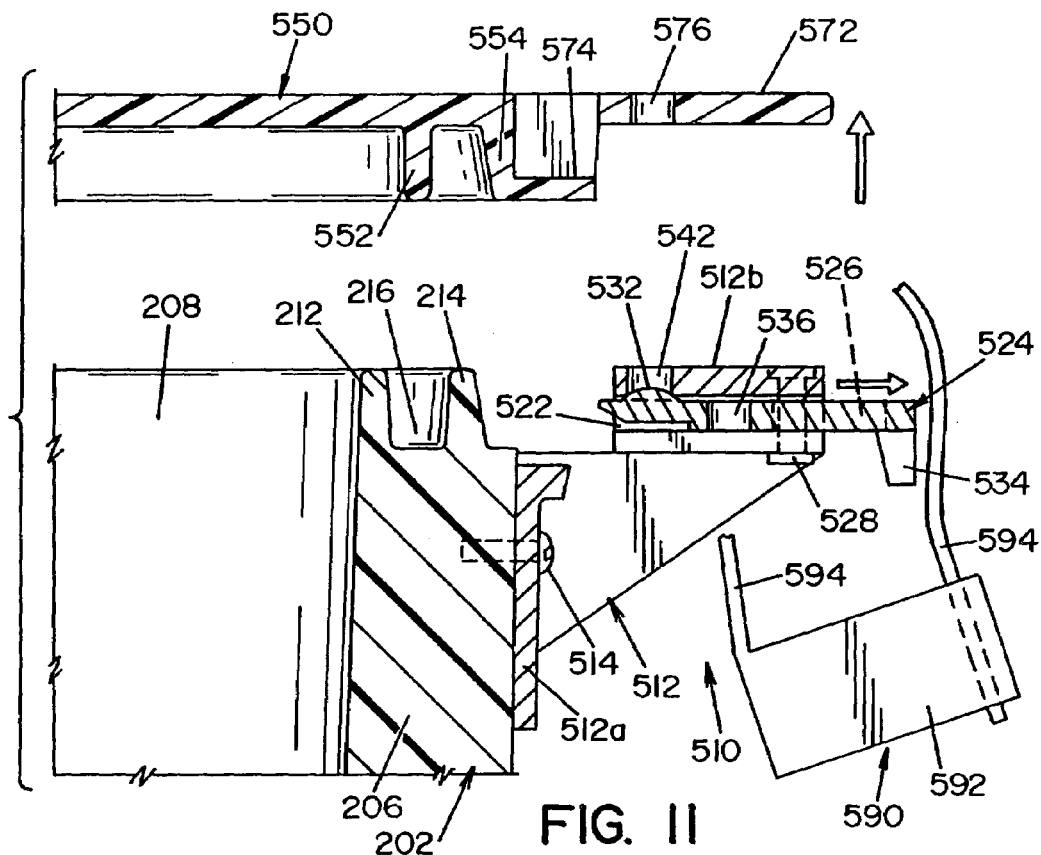
FIG. 11 is an enlarged view of the lid and container portions shown in FIG. 10, showing a locking arrangement in an opened configuration.

Referring now to FIGS. 3, 10 and 11, handle assemblies 510 are provided at the ends of tray 202 are best seen. Each handle assembly 510 includes a handle bracket 512 having a mounting portion 512a for attachment to side wall 206 of tray 202 by conventional fasteners 514, as illustrated in the drawings. A handle or grip portion 512b extends from mounting portion 512a. Coplanar, spaced-apart slots 522, best seen in FIG. 3, are formed along the lateral end of handle portion 512b to slidably receive a generally planar latch element 524. Latch element 524 is dimensioned to slide within slots 522 of handle portion 512b. Pins or fasteners 528 extend through handle portions 512b into elongated openings 526 in latch 524 to allow a limited portion of latch 524 to slide within handle portion 512b. Latch 524 includes a bump or dimple 532 formed on the upper surface of one end thereof and a tab 534 formed on the bottom surface at the opposite edge of latch 524. Latch 524 includes an aperture 536 that is alignable with an aperture 542 in handle portion 512b. Latch 524 is provided to lock lid 550 onto tray 202.

Lid 550, best seen in FIG. 3, is generally a planar element that is shaped to enclose the opened, upper end of tray 202. Lid 550 includes a pair of downwardly extending, generally continuous rails or wall sections 552, 554 that extend along the periphery of lid 550. Wall sections 552, 554 are dimensioned to be disposed in mating contact with rails 212, 214 on the upper edge of side wall 206 of tray 202, as best seen in FIGS. 10 and 11. As illustrated in FIGS. 10 and 11, wall sections 552, 554 on lid 550 are slightly shorter than rails 212, 214 that extend from the upper edge of side wall 206, wherein lid 550 essentially rests upon the upper edges of rails 212, 214 of side walls 206 of tray 202. A U-shaped gap or space 562 is defined between the downwardly extending wall sections 552, 554 of lid 550 and rails 212, 214 and the upper surface of side wall 206. The interlocking arrangement between lid 550 and tray 202 defines a novel type of seal assembly, as shall be described in greater detail below.

Lid 550 includes an extension portion 572 that is dimensioned to overlay handle assembly 510 on tray 202. A ledge or lip 574 is formed on extension portion 572. Lip or ledge 574 is dimensioned to be disposed in general alignment with handle portion 512b of handle assembly 510 wherein latch element 524 may be moved to a locking position wherein latch element 524 is disposed over lip or ledge 574 of lid 550. In this position, latch element 524 captures ledge 574 between latch element 524 and handle assembly 510 thereby locking lid 550 in position onto tray 202. Extension portion 572 of lid 550 also includes an aperture 576 that is positioned to be aligned with apertures 542 within handle portion 512b of handle assembly 510, and aperture 536 in latch element 524 when latch element 524 is in a locked or latched position.

In accordance with another aspect of the present invention, a locking device 590 is provided to secure lid 550 to tray 202. Locking device 590 is comprised of a body portion 592 and an elongated, flexible arm portion 594 that extends therefrom. Arm portion 594 is dimensioned to be able to extend through apertures 576, 536 and 542 in lid 550, latch 524 and handle portion 512b and inserted back into body 592, in a manner similar to conventional tie-lock bands. In this respect, body portion 592 and elongated arm portion 594 are preferably integrally formed of a moldable plastic material, wherein the end of arm portion 594 may be inserted into an opening in body portion 592, but may not be removed once inserted therein. Arm portion 594 is preferably dimensioned to be relatively easily broken by movement of latch element 524 away from the latching position, as shall be described in greater detail below.

Figure 16:
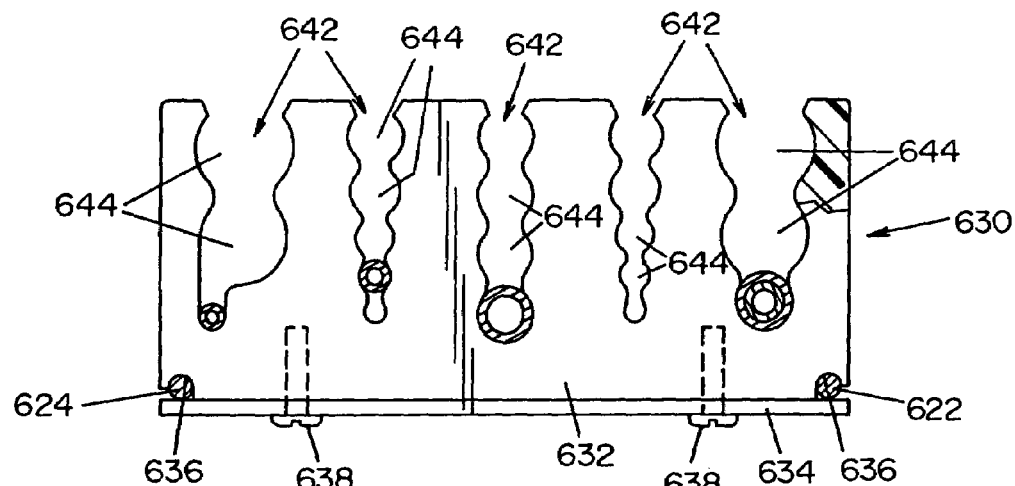
FIG. 16 is an enlarged, elevational view of a mounting block assembly for holding portions of the items to be microbially deactivated.

Referring now to FIGS. 14–18, an instrument holder 610 for use within container 200 for organizing and positioning items, such as medical instruments, for microbial deactivation is best seen. In the embodiment shown, instrument holder 610 is basically comprised of a base section 612 (best seen in FIG. 15) and an upper section 652 (best seen in FIG. 17). Base section 612 is basically comprised of a wire frame 614 that is formed to support a perforated panel 616 that is disposed at one end of frame 614. Panel 616 is surrounded by a generally U-shaped rail 618. Frame 614 includes two parallel, spaced-apart frame members 622, 624. An upturned stop 626 is formed at one end of frame 614. Frame 614 includes instrument holder 630 that is dimensioned to be attached to frame members 622, 624. Each instrument holder 630 is comprised of an instrument mounting block 632 and a plate 634 that is attachable to block 632. As best seen in FIG. 16, block 632 includes cylindrical grooves 636 formed along the bottom edges thereof, wherein frame members 622, 624 of base section 612 may be captured between block 632 and plate 634 of instrument holder 630. Conventional fasteners 638 are used to attach plate 634 to mounting block 632 and to secure instrument holder 630 to frame members 622, 624, as best seen in FIG. 16.

Mounting blocks 632 are preferably formed of a generally rigid, polymeric material and include a plurality of slots 642 having predetermined profiles. Slots 642 are generally defined by a plurality of aligned, side-by-side, overlapping circular areas 644. Slots 642 have an opened upper end and a closed lower end, and side walls that converge toward each other from the open end to the closed end. Circular areas 644 are preferably designed to receive a plurality of objects of varying circular diameter, namely tubular portions of medical instruments, as illustrated in FIG. 16.

Figure 14:
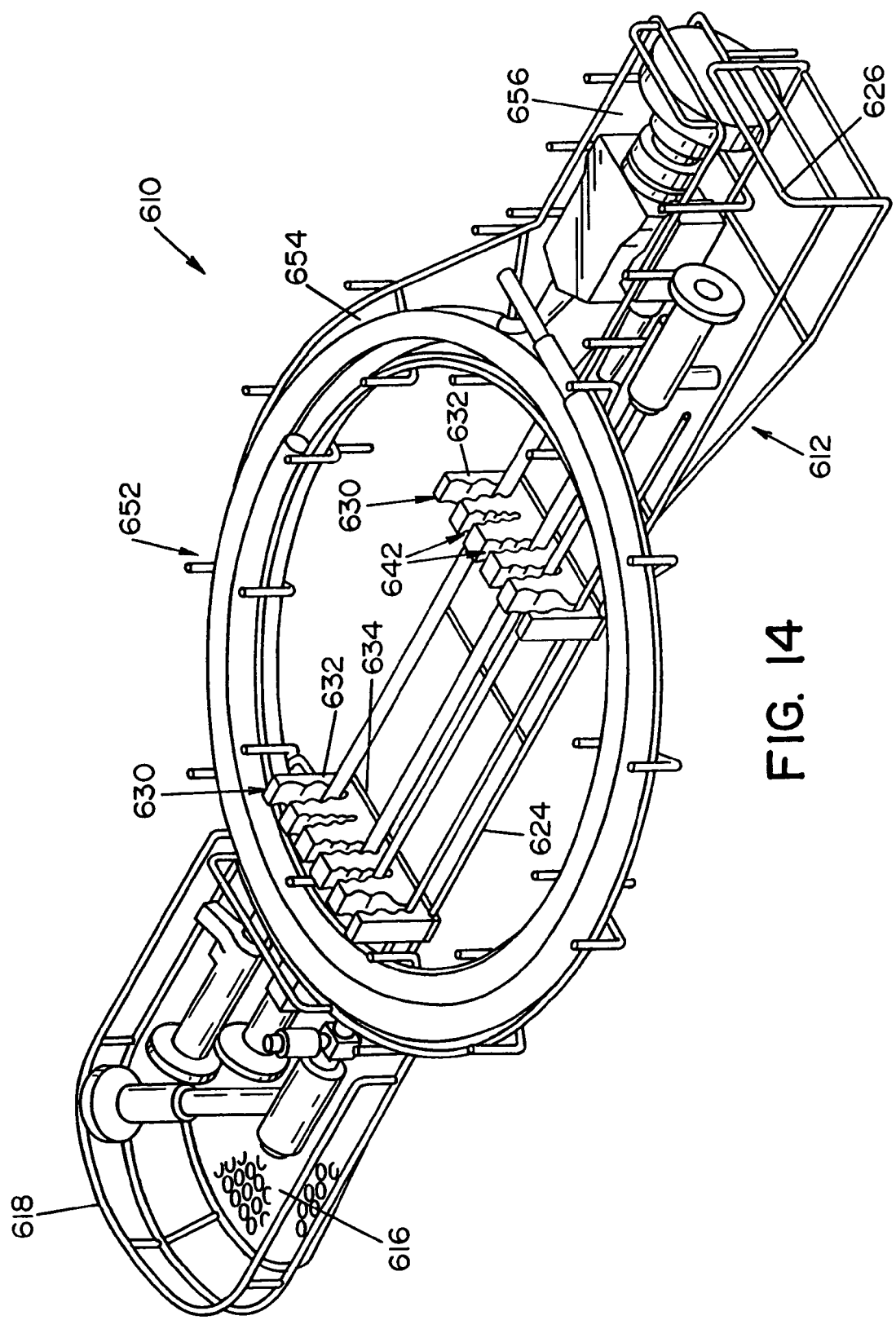
FIG. 14 is a perspective view of a rack assembly for holding items to be deactivated, showing medical instruments mounted thereon.
Figure 15:
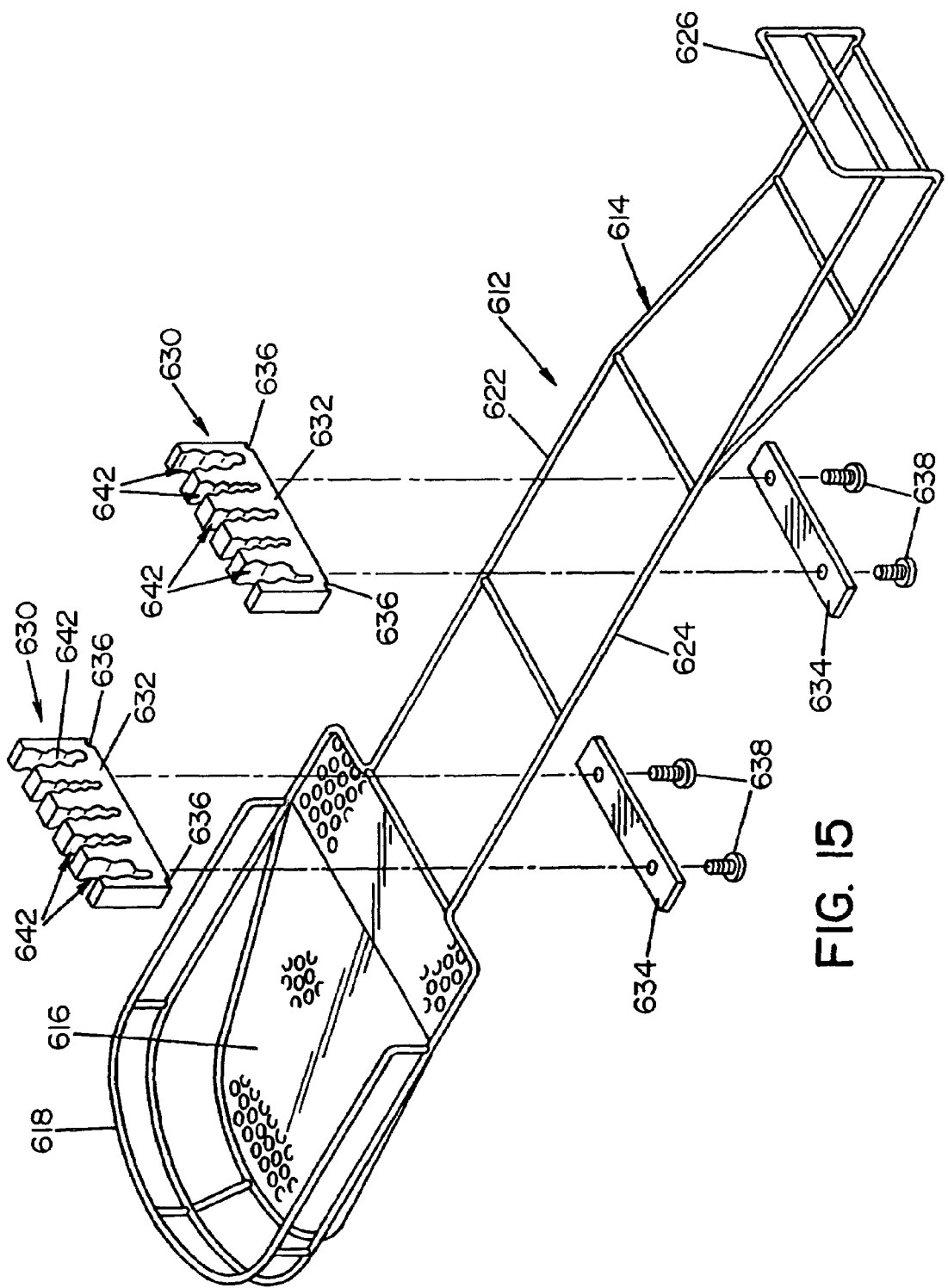
FIG. 15 is perspective view of a base section of the tray assembly shown in FIG. 14, showing mounting blocks exploded therefrom.
Figure 17:
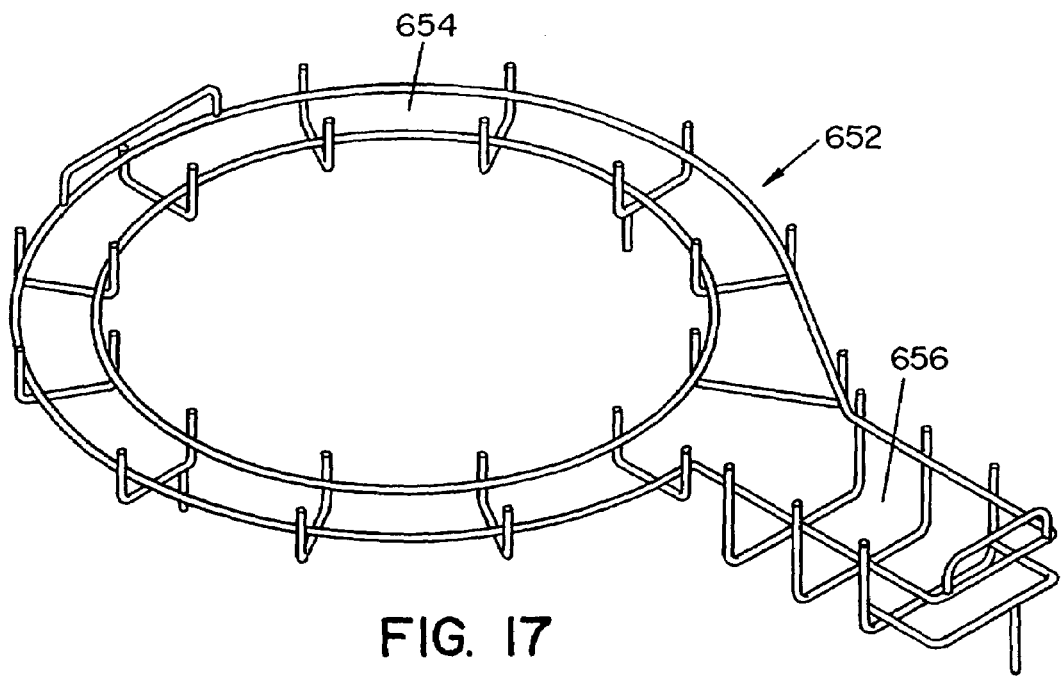
FIG. 17 is a perspective view of an upper section of the tray assembly shown in FIG. 14.

Referring now to FIG. 17, upper section 652 is best seen. Upper section 652 is basically a wire, rack or tray that is formed to have an annular holding area 654 and a rectangular holding area 656. Upper section 652 is designed to nest and mate with lower base section 612, as illustrated in FIG. 14.

Figure 18:
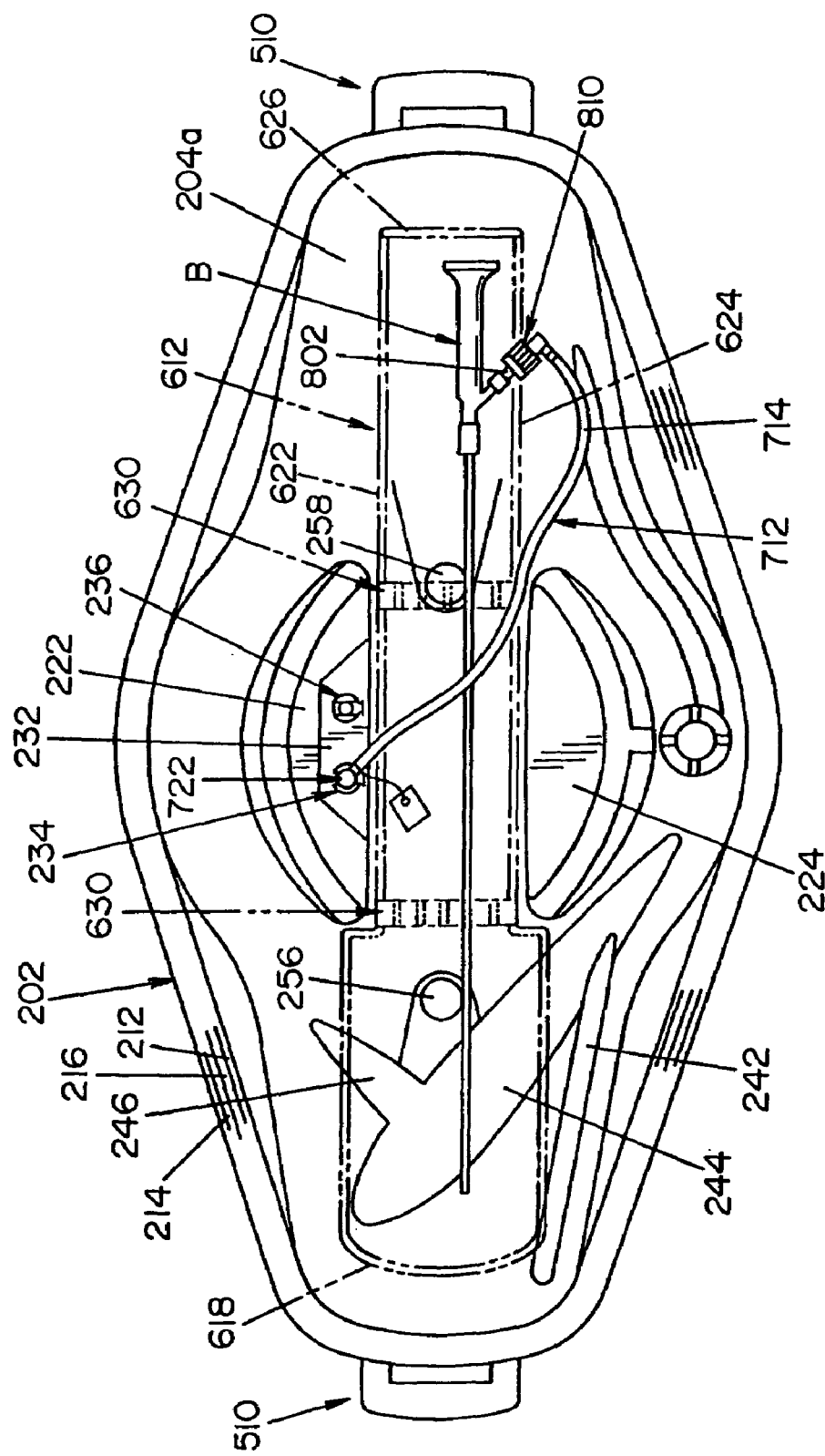
FIG. 18 is a top plan view showing a medical instrument within the container, and illustrating a flush tube connected to the medical instrument.

Referring now to FIG. 18, a system for deactivating lumens and passages within a medical device is illustrated. FIG. 18 shows tray 202 with a bronchoscope B positioned within instrument holder 630 (shown in phantom). A flexible connector 712 is attached at one end to connector fitting 234 in relief or recess 232 of mounting block 222, and the other end of flexible connector 712 is attached to a fitting on medical instrument B. Flexible connector 712 is attached to connector fitting 234 on tray 202 to define a microbial deactivation fluid flow path to the lumens in medical instrument B. Flexible connector 712 includes a length of medical-grade tubing 714 having a male fitting 722 (best seen in FIG. 19) at one end, and a link assembly 810 (best seen in FIGS. 20–22) at the other end for attachment to medical instrument B.

Figure 19:
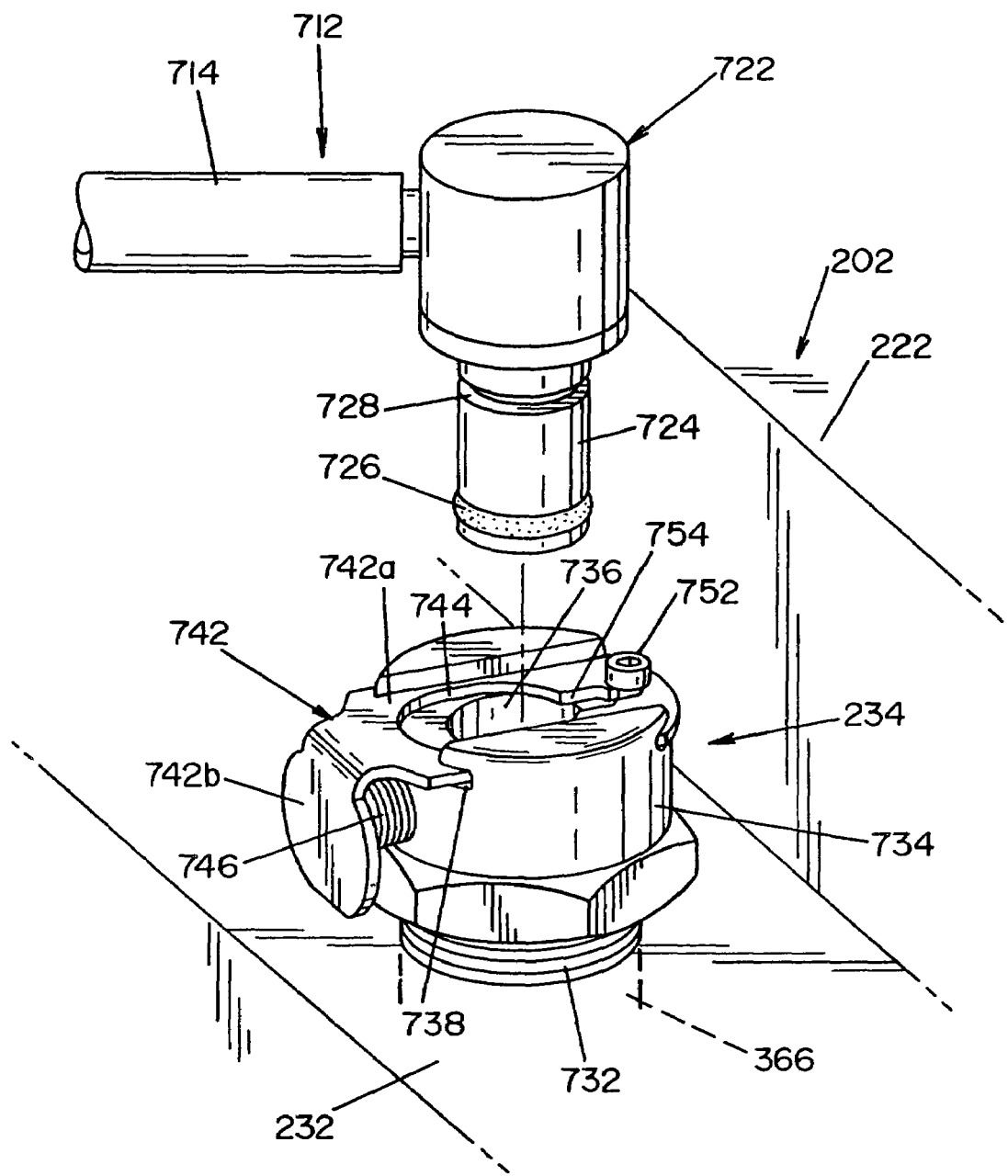
FIG. 19 is an enlarged, perspective view showing a connector on one end of the lumen flush tube, illustrating a connector assembly for attaching the lumen flush tube to the container.

Referring now to FIG. 19, male fitting 722 for attaching flexible connector 712 to tray 202 is shown. Fitting 722 includes a cylindrical portion 724 for insertion into connector fitting 234 that is attached to mounting block 222. Cylindrical portion 724 includes an O-ring 726 mounted within a groove that is formed in cylindrical portion 724 near the free end thereof. An annular slot 728 is formed in cylindrical portion 724 above O-ring 726. An internal bore or passage (not shown in the drawings) is formed through cylindrical portion 724 and male fitting 722 to be in communication with the passage defined by tubing 714.

Connector fitting 234 that is attached to mounting block 222 is basically a female connector having a threaded portion 732 for threaded insertion into a bore mounting pad 222. Connector fitting 234 has a body portion 734 with an opening 736 extending therethrough in fluid communication with opening 366 in bottom wall 204 of tray 202. A slot 738 is formed through the upper end of connector body 734 to receive a lock element 742 in sliding fashion. Lock element 742 has planar portion 742a dimensioned to be received within slots 738 formed in connector body 734. A circular opening 744 is formed in planar portion 742a of locking element 742. Locking element 742 also includes a thumb portion 742b that is disposed at a right angle to planar portion 742a of locking element 742. A biasing element 746, that in the embodiment shown is a helical spring, is disposed between the thumb portion 742b of locking element 742 and connector body 734. Biasing element 746 is operable to bias thumb portion 742b away from connector body 734. Locking element 742 is maintained in connector body 734 by cap screw 752 that extends through a slot 754 in planar portion 742a of locking element 742. As shown in FIG. 19, slot 754 in planar portion 742a of locking element 742 communicates with circular opening 744 therein. Locking element 742 is moveable by depressing thumb portion 742b to a first position, wherein circular opening 744 in locking element 742 is aligned with bore 736 in connector body 734. With locking element 742 in this position, cylindrical portion 724 of male fitting 722 is inserted through circular opening 744 in locking element 742 into bore 736 in connector body 734. With cylindrical portion 724 of fitting 722 within bore 736 of connector body 734, release of thumb portion 742b causes locking element 742 to slide into annular slot 728 formed within cylindrical portion 724, thereby locking fitting 722 into connector body 734. In the embodiment shown, connector fitting 234 is a fitting manufactured by Colder Products Company of St. Paul, Minn.

Referring now to FIG. 20, link assembly 810 is best seen. Link assembly 810 is provided to attach flexible connector 712 to a fitting 802, best seen in FIG. 22 on medical instrument B, to be deactivated. Link assembly 810 includes an elbow fitting 812 having a first end 812a that is dimensioned to receive tubing 714. A hose or tube clamp 814 locks tubing 714 onto first end 812a of elbow fitting 812. A second end 812b of elbow fitting 812 is attached to a sleeve 822. Sleeve 822 is generally cylindrical in shape and has an inwardly extending annular wall 822a. An outwardly extending annular flange 816 is formed at second end 812b of elbow fitting 812. Flange 816 on elbow fitting 812 is captured and maintained against annular wall 822a of sleeve 822 by a retaining ring 824. Inwardly extending annular wall 822a of sleeve 822 defines an opening 826 that communicates with the opening through elbow fitting 812. The inner edges of annular wall 822a and the opening of elbow fitting 812 are preferably champhered, as shown in the drawings.

A cylindrical collar 832 is fixedly attached to the end of sleeve 822. Collar 832 has internal threads 832a that are dimensioned to match external threads on fitting 802 on medical instrument B. A tubular valve element 842 is disposed between sleeve 822 and collar 832. Valve element 842 defines a passage 842a therethrough. Valve element 842 has a generally L-shaped annular wall 844 extending outwardly from the mid-section thereof. Annular wall 844 defines an annular recess 846 around valve element 842. A biasing element 848, in the form of a helical spring, is disposed in recess 846 between L-shaped annular wall 844 of valve element 842 and inwardly extending annular wall 822a of sleeve 822. Biasing element 848 is operable to bias valve element 842 away from opening 826 in sleeve 822. A pin 852 embedded within valve element 842 extends into a slot 854 that is formed along the inner surface of sleeve 822. Pin 852 and slot 854 maintain the position of valve element 842 relative to sleeve 822, and guides valve element 842 within sleeve 822. Notches or openings 862 are formed in L-shaped annular wall 844 of valve element 842. Notches or openings 862 in L-shaped annular wall 844 are aligned with openings 864 that are formed through sleeve 822.

When not attached to a medical instrument, link assembly 810 assumes a first position, as seen in FIG. 20, wherein valve element 842 is biased away from elbow fitting 812 and the passage that is defined therethrough. In this respect, a portion of any fluid flowing through flexible connector 712 would flow through passage 842a in valve element 842, but have another portion that would bypass valve element 842 and flow around valve element 842, and flow through notches 862 and openings 864 in L-shaped annular wall 844 and sleeve 822, respectively.

When properly attached to fitting 802 of medical instrument B, valve element 842 assumes a second position, wherein one end of valve element 842 is seated against the surface of elbow fitting 812, and the other end of valve element 842 is seated against fitting 802 on medical instrument B. Fluid flowing through flexible connector 712 is thus directed only through passage 842a in valve element 842 and into the passage within fitting 802 on medical instrument B, and thus flows through the lumens and passageways within medical instrument B.

Apparatus 10 shall now further be described with reference to the operation thereof. One or more items to be deactivated, such as medical, dental, pharmaceutical, veterinary or mortuary instruments or other devices are loaded into container 200. Certain items may be placed within instrument holder 610, as shown in FIG. 14, while other items may be set in the bottom of tray 202, resting within surface recesses 242, 244, 246 and 248 therein.

In this respect, container 200 can accommodate numerous types of medical instruments and other items. Certain medical instruments include lumens, i.e., passages, that extend therethrough. Instruments, such as bronchoscopes and endoscopes, are preferably set into instrument holder 610, wherein elongated, flexible tubes on such devices may be placed into annular holding area 654 of upper section 652, as shown in FIG. 14. Flexible connectors 712 are used to connect fluid passages 366 on tray 202 to internal lumens of the medical instruments. More specifically, flexible connectors 712 are dimensioned such that link assemblies 810 fit onto fittings on the medical instruments so as to enable microbial deactivation fluid to be forced through the lumens of the medical instruments. The medical instrument would be set within instrument holder 610 and link assemblies 810 of flexible connectors 712 that would be attached to tray 202 using connector fittings 234, 236. Link assemblies 810 on flexible connector 712 are then attached to the port(s), i.e., fittings, on the medical device. As shall be described in greater detail below, a deactivation cycle would not be performed if a male connector assembly is attached to a female connector assembly unless link assemblies 810 on flexible connector 712 are properly connected to the fittings on the medical instruments.

Once flexible connector(s) 712 have been attached to tray 202 and to the medical instrument, lid 550 is placed over tray 202. As best illustrated in FIGS. 8–11, upwardly extending rails 212, 214 of side wall 206 of tray 202 interact with spaced-apart walls 552, 554 on lid 550, as shown in FIGS. 8–10. As indicated in FIGS. 8–10, lid 550 essentially rests on the upper ends of rails 212, 214 on side wall 206. In this respect, as shown in the drawings, wall members 552, 554 of lid 550 are slightly shorter than rails 212, 214 on side wall 206 such that generally U-shaped passage 562, best seen in FIG. 10, extends around container 200 between the mating periphery of lid 550 and side wall 206. A convoluted, generally serpentine passage is thus defined between lid 550 and the upper edge of side wall 206. The serpentine passage extends between the interior of container 200 to the exterior of container 200.

With lid 550 properly positioned upon tray 202, lid 550 is locked into position by sliding latch element 524 on handle assembly 510 over ledge 574 on lid 550, as best seen in FIG. 10.

In accordance with one aspect of the present invention, once the instruments or items to be microbially deactivated are placed within tray 202 and lid 550 has been attached and latched thereto, locking device 590 is attached to extension portion 572 of lid 550 and to handle assembly 510, as best seen in FIG. 10, to prevent lid 550 from being removed from tray 202. As indicated above, in a preferred embodiment of the present invention, locking device 590 is preferably a polymer strap that is lockable onto itself. With the contaminated instruments within container 200 and locking device 590 attached thereto, container 200 is placed within deactivation chamber 50. In this respect, first and second fluid inlet assemblies 340, 360 and outlet fluid assembly 280 are aligned with valve actuating connectors 410 on panel 14 to connect container 200 and the fluid passages therein to first and second branch feeder lines 92, 94 and branch return line 106 of fluid circulation system 60, as schematically illustrated in FIG. 2. Chemical delivery container 34 is then placed in receiving well 32 in apparatus 10. Lid 42 of apparatus 10 is then closed and latched thereby sealing deactivation chamber 50.

FIGS. 12 and 13 show how valve actuating connectors 410 on panel 14 interact with valve elements 312 of fluid inlet assemblies 340, 360 and fluid outlet assembly 280 to place the interior of container 200 in fluid communication with the respective branch feeder lines 92, 94 and return line 106. More specifically, pin 454 on actuating connector 410 pushes valve element 312 on an associated fluid assembly 280, 340, 360 to move the same from its sealing position to its opened position. In other words, once container 200 is set into place and interacts with corresponding actuating connectors 410, branch inlet lines 92, 94 are in fluid communication with the interior of container 200, and branch return line 106 is in fluid communication with the interior of container 200.

The items are microbially deactivated with a microbial deactivation fluid, such as a peracetic acid fluid, which in a preferred embodiment, is formed by exposing and mixing dry chemical reagents within chemical delivery container 34 with incoming water. In this respect, at the beginning of a deactivation operation, drain valve 122 in fluid circulation system 60 is closed, and valve 72 in water inlet line 62 is opened to allow heated water to enter fluid circulation system 60. Incoming water is first filtered by filter elements 64, 66 that remove macro particles above a certain size, such as 0.1 micron ($\mu$) or above. Filter elements 64, 66 are sized to successively filter out smaller sized particles. Incoming water is then treated by UV treatment device 68 that applies ultra-violet (UV) radiation to the water to reduce the level of viruses therein. The incoming water then passes valve 72 and enters fluid circulation system 60. The incoming water is then filtered by micro filter elements 84, 86 in system feeder line 82, and proceeds to fill fluid circulation system 60, deactivation chamber 50, and container 200. All of the incoming water preferably flows through filter elements 84, 86, thereby insuring filtration of the water flowing into apparatus 10.

The incoming water is under pressure from an external source, and forces air in fluid circulation system 60, deactivation chamber 50 and container 200 that is preferably disposed at the highest point of apparatus 10. As a result of water entering apparatus 10, air within the system will migrate toward air inlet/fluid overflow assembly 132.

The presence of the water flowing through air inlet/fluid overflow assembly 132 is indicative that apparatus is filled. The system controller then causes water valve 72 to close, thereby stopping the flow of water into apparatus 10, i.e., into fluid circulation system 60, deactivation chamber 50 and container 200.

The foregoing description basically describes a water fill phase of apparatus 10.

Figure 4:
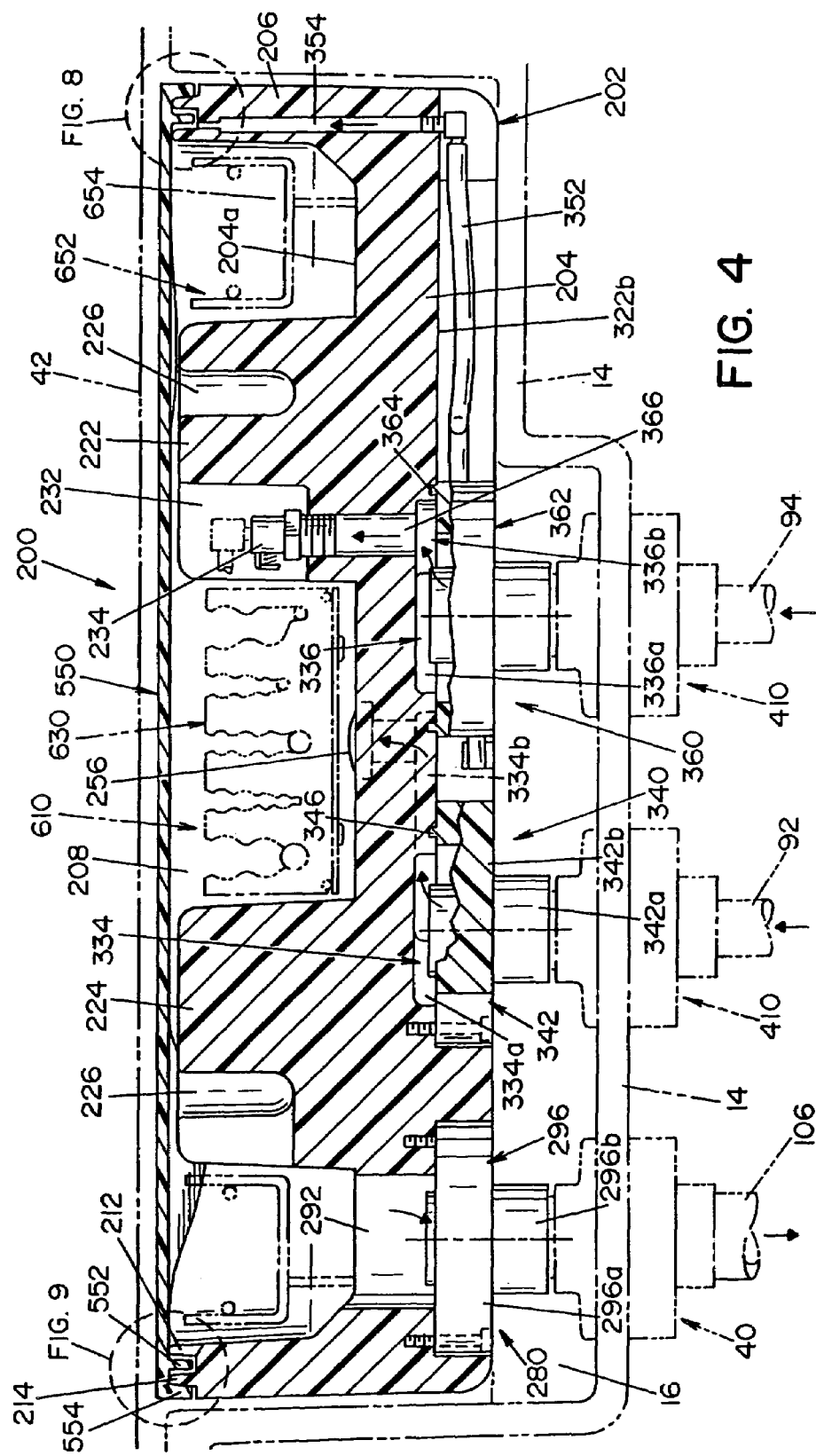
FIG. 4 is a sectional view taken along lines 4—4 of FIG. 1.

Once apparatus 10 is filled with water, the system controller initiates a generation and exposure phase of operation, wherein pump 116 is energized to circulate water through fluid circulation system 60, deactivation chamber 50 and container 200. Valve 102 in second branch feeder line 94 is opened to create flow through chemical delivery container 34. The water and dry chemical reagents within chemical delivery container 34 form a microbial deactivation fluid that, as indicated above, in a preferred embodiment of the invention, is peracetic acid. The deactivation fluid formed from the dry chemical reagents flows into fluid circulation system 60, wherein it is circulated through fluid circulation system 60, deactivation chamber 50 and container 200 by the operation of pump 116. As indicated in the drawings, a portion of the microbial deactivation fluid flows into deactivation chamber 50 around container 200, and a portion of the microbial deactivation fluid flows into and through container 200 and the items contained therein. The microbial deactivation fluid flowing through branch feeder line 92 into first fluid inlet assembly 340 is directed through passages within container 200 to spray nozzles 256, 258, as best seen in FIG. 5. The microbial deactivation fluid is thus forced into interior cavity 208 of container 200 to fill the same. In one embodiment of the present invention, a portion of the microbial deactivation fluid flowing into first fluid inlet assembly 340 is directed through passage 354 in side wall 206 into U-shaped gap 562 defined between container 200 and lid 550, as best seen in FIG. 4. In this respect, a portion of the microbial deactivation fluid flowing into container 200 is directed through tube 352 to the interface between lid 550 and tray 202 via passage 354 through side wall 206, as shown in FIG. 8. The microbial deactivation fluid flows through U-shaped gap 562 between lid 550 and the upper edge of side wall 206 to the opposite side of tray 202 where it is allowed to enter interior cavity 208 of tray 202 through opening 218 defined in innermost rail 212 on side wall 206, as shown in FIG. 9. Basically, microbial deactivation fluid is forced into the seal region where it flows throughout the seal thereby deactivating the convoluted, serpentine passage defined between container 200 and lid 550.

The microbial deactivation fluid flowing into second fluid inlet assembly 360 is directed to the lumens of the medical instrument through flexible connector 712, as described above. The microbial deactivation fluid flowing through container 200 is returned to pump 116 via branch fluid return line 106 and system return line 112. Microbial deactivation fluid flowing through deactivation chamber 50 returns to pump 116 via branch fluid return line 108 and system return line 112. Microbial deactivation fluid flowing through chemical delivery container 34 returns to pump 116 via branch fluid return line 104 and system return line 112. Pump 116 continuously re-circulates the microbial deactivation fluid through fluid circulation system 60 for a predetermined period of time that is sufficient to decontaminate items within container 200 and in addition to decontaminate the components and fluid conduits of fluid circulation system 60.

After a predetermined exposure period, the system controller initiates a drain phase, wherein drain valve 122 is opened and the microbial deactivation fluid is drained from fluid circulation system 60, deactivation chamber 50 and container 200.

After the microbial deactivation fluid has been drained from apparatus 10, one or more rinsing phases are performed to rinse any residual microbial deactivation fluid and any residual matter from the deactivated items within container 200. In this respect, inlet valve 72 is opened to introduce fresh water into apparatus 10, in a manner as heretofore described as the fill phase. After each rinse fill, the rinse water is drained from apparatus 10 as heretofore described. Pump 116 may be activated to circulate the rinse water through apparatus 10. During each fill, circulation and drain phase, fluid over-flow/air make-up assembly 132 operates to prevent bio-contaminants from entering the internal environment within apparatus 10.

In the embodiment shown, the circulated deactivation fluid flows through filter elements 84, 86. The amount of fluid flowing through the respective portions of the system may be controlled by regulating valves disposed within fluid circulation system 60. The microbial deactivation fluid flowing through filter feed line 82 and through filter elements 84, 86 are to insure deactivation of filter elements 84, 86 by exposure to the microbial deactivation fluid. In this respect, the flow of the deactivation fluid through filter elements 84, 86 deactivates the same and deactivates any bio-contamination that may have entered into filter elements 84, 86 during the water fill cycle. Thus, during each operation of apparatus 10, filter elements 84, 86 are exposed to a deactivation fluid to deactivate same. Bypass line 76, best seen in FIG. 2, controls the amount of chemicals flowing through filter elements 84, 86. As indicated above, the microbial deactivation fluid flows throughout the closed-loop, fluid circulation system 60 during a deactivation phase, thereby decontaminating fluid circulation system 60, and the components and fluid conduits forming the same. In other words, fluid circulation system 60 is decontaminated during each decontamination cycle.

Once the deactivation phase has been completed, lid 42 of apparatus 10 may be opened and container 200 with the deactivated instruments therein may be removed. Fluid assemblies 280, 340 and 360 move to a closed position when container 200 is removed from apparatus 10, thereby preventing microbial contamination of the interior of container 200.

In accordance with one aspect of the present invention, the deactivated instruments can remain in container 200 as a sort of deactivated packaging, and may be stored on a shelf for a prolonged period of time, with the instruments therein remaining in a microbially deactivated environment due to the lack of exposure to the surrounding environment. In this respect, the only way for the atmosphere to enter container 200 is through the tortuous path defined by rails 212, 214 and wall sections 552, 554 of tray 202 and lid 550, respectively. In this respect, it has been found that such a design prevents migration of bacteria or organisms along the serpentine, U-shaped gap 562 due to the microbially deactivated conditions therein.

Still further, it is believed that notwithstanding an air blow off phase to force fluid from container 200, that the interior of container 200 will remain somewhat "damp" therein. The damp interior of container 200 may be dried in a low heat oven, wherein the moisture would be driven from the interior of container 200 over time. Locking devices 590 on lid 550 and tray 202 provide an indication that the instruments therein are microbially deactivated when locking devices 590 are intact, indicating that container 200 has not been opened.

When a microbially deactivated instrument is needed for use, lid 550 may be removed by simply sliding latching element 524 away from its locking position.

Figure 23:
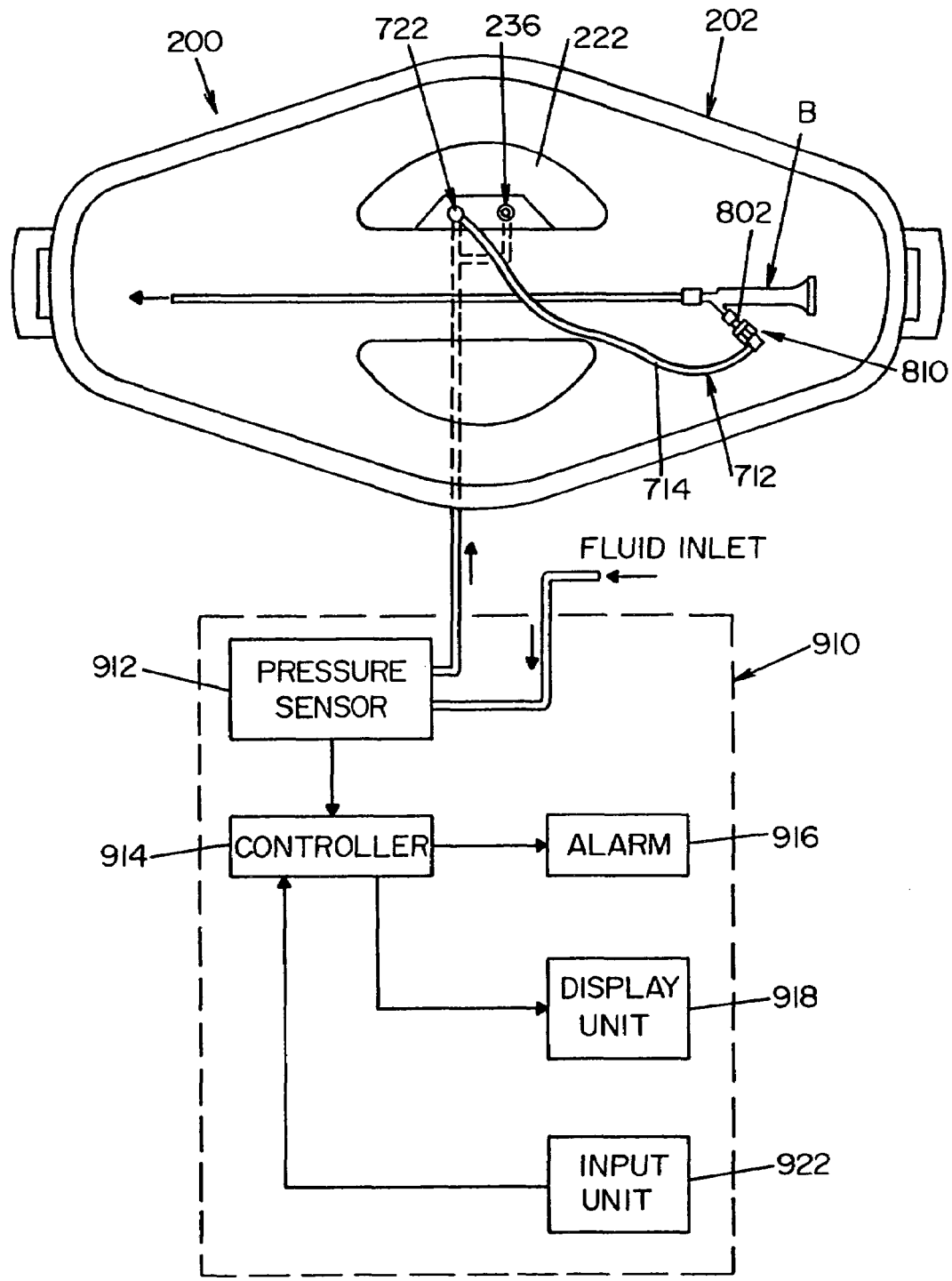
FIG. 23 is a top plan view of a container according to the present invention and a monitoring system that is schematically illustrated therewith.

Referring now to FIG. 23, a block diagram illustrating a monitoring system 910 for ensuring proper connection of link assemblies 810 to fittings 802 on medical instrument B is shown. Monitoring system 910 is generally comprised of a pressure sensor 912, a controller 914, an alarm 916, a display unit 918, and an input unit 922.

Pressure sensor 912 measures the pressure of the microbial deactivation fluid flowing through second fluid inlet assembly 360 to flexible connector(s) 712. Pressure sensor 912 outputs an electrical signal indicative of a sensed fluid pressure value. This electrical signal is received by controller 914, as described below. In a preferred embodiment, pressure sensor 912 takes the form of a pressure transducer.

Controller 914 is preferably the system microprocessor or microcontroller used to control other system operations and components. Controller 914 is programmed to determine whether each flowable link assembly 810 on flexible connector 712 has been properly connected within container 200, based upon the electrical signal indicative of the sensed fluid pressure value, as will be described in further detail below. An alarm 916, that preferably takes the form of an audio generating means (e.g., a speaker) for generating an audible signal, is provided to alert the operator to an error condition, namely, the improper connection of the tubing.

A display unit 918 provides a means for visually communicating with an operator. In a preferred embodiment, display unit 918 takes the form of an LCD or LED display.

Input unit 922 provides a means for the operator to enter data into controller 914. In a preferred embodiment, input unit 922 takes the form of a conventional keypad or keyboard.

Figure 22:
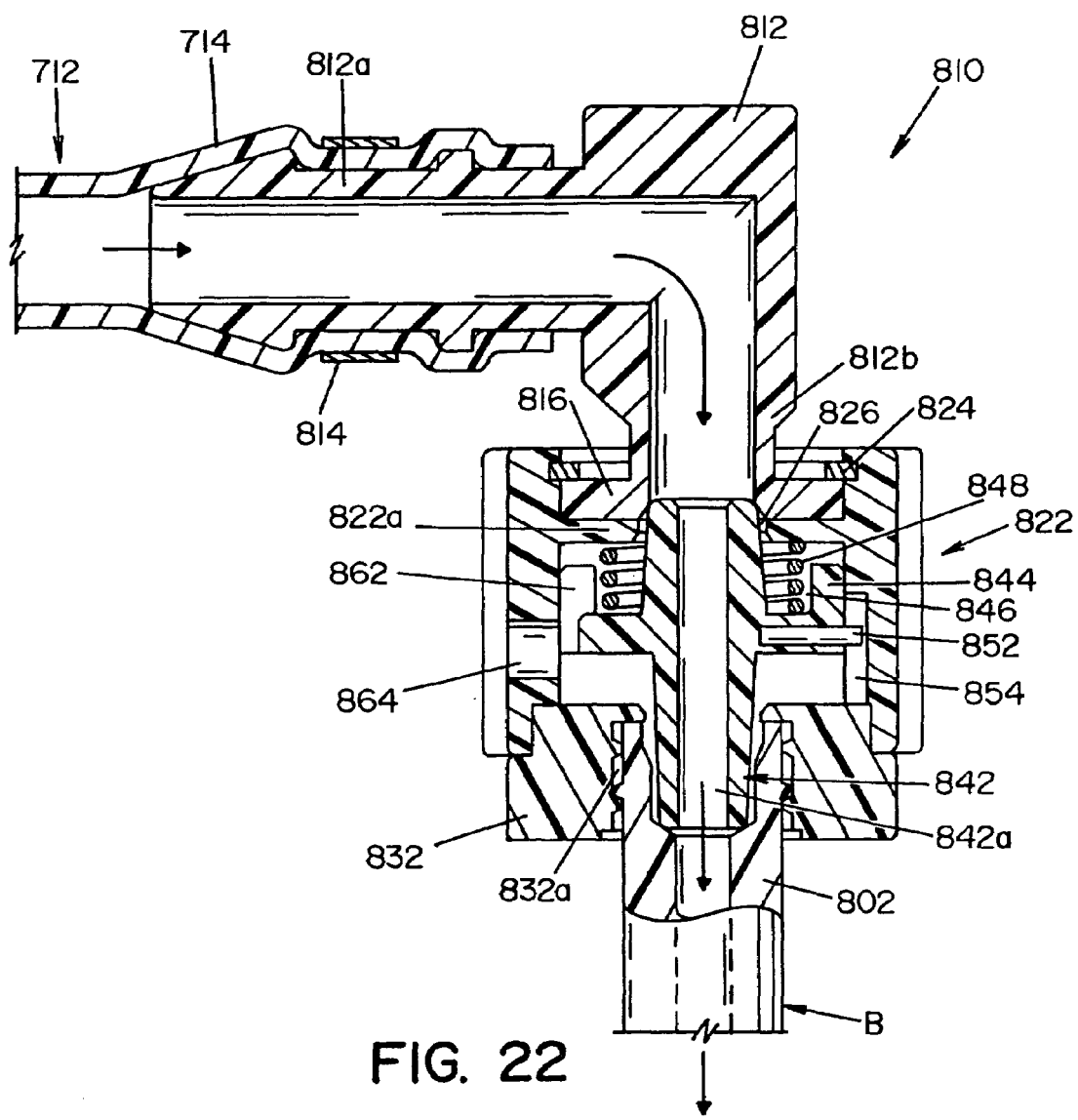
FIG. 22 is a sectional view of the fitting shown in FIG. 20 attached to a portion of a medical instrument.

Operation of monitoring system 910 shall now be described in detail. As indicated above, pressure sensor 912 measures the pressure of the microbial deactivation fluid flowing through second fluid inlet assembly 360 to flexible connector 712. Pressure sensor 912 outputs an electrical signal indicative of a sensed fluid pressure value that is received by controller 914. Controller 914 is programmed to determine whether the sensed fluid pressure value (received from pressure sensor 912) is indicative of a predetermined pressure value associated with proper connection of a flowable link assembly 810 on flexible connector 712 to fitting 802 on medical instrument B. For instance, controller 914 may compare the sensed fluid pressure value to the predetermined pressure value. If the comparison indicates a significant deviation from the predetermined pressure value, controller 914 determines that an improper connection to medical instrument B exists in container 200. An improper connection may be the result of a link assembly 810 not being properly connected to a fitting 802 on a medical instrument. FIG. 22 shows a link assembly 810 that is properly connected to a matching fitting 802 on a medical instrument (not shown in FIG. 22). When link assembly 810 is connected to the medical device as shown, valve element 842 is snuggly seated against elbow fitting 812 and fitting 802. All of the microbial deactivation fluid flowing through flexible connector 712 is forced into the lumens of the medical device and would establish the predetermined pressure value.

If link assembly 810 is not securely connected to fitting 802, or if link assembly 810 does not match fitting 802 on the medical instrument, valve element 842 will not be properly seated against elbow fitting 812 or fitting 802, thereby allowing fluid to flow around valve element 842 through opening 864 in sleeve 822 or between fitting 802 and sleeve 822. This condition would result in a pressure lower than the predetermined pressure value being sensed by pressure sensor 912, the lower pressure being an indication of a faulty connection between flowable flexible connector 712 and the medical instrument. Likewise, if the system controller determines that a connection is to be made, a lower than expected pressure may be an indication that male fitting 722 on flexible connector 712 is not properly attached to connector fitting 234 or 236 on tray 202.

Furthermore, the improper connection may be the result of only one of two flowable flexible connectors 712 being attached to a medical instrument, when two flexible connectors 712 must be connected to two ports on one or more medical devices. It should be appreciated that a lower pressure will be sensed when there is an improper flowable connection.

In a preferred embodiment, detection of an improper connection results in controller 914 activating alarm 916 to produce an audible warning signal to the operator, and controlling display unit 918 to: (a) display a graphic indicating the location within apparatus 10, and specifically container 200, where an improper connection has been detected, and (2) provide visual and/or written instructions as to how to correct the improper connection. The operator may also be queried as to whether he wishes to proceed with a deactivation cycle, or abort the current deactivation cycle.

It should be appreciated that more than one pressure sensor 912 may be used. In this regard, pressure sensor 912 may be associated with each flexible connector 712.

The foregoing description is a specific embodiment of the present invention. It should be appreciated that this embodiment is described for purposes of illustration only, and that numerous alterations and modifications may be practiced by those skilled in the art without departing from the spirit and scope of the invention. Specifically, although the present invention has been described with respect to a reprocessor utilizing a microbial deactivation fluid, it is contemplated that the present invention be used in reprocessing systems wherein a gas or vapor microbial deactivation fluid is used. It is intended that all such modifications and alterations be included insofar as they come within the scope of the invention as claimed or the equivalents thereof.

Having described the invention, the following is claimed:

1. A container for holding items to be microbially deactivated in a reprocessor, comprised of:
   a generally cup-shaped tray having a bottom wall and a continuous side wall extending to one side from the periphery of said bottom wall, said side wall having a free edge, said bottom wall and said side wall defining a cavity for receiving instruments and items to be microbially deactivated;
   a rigid first seal element formed along said free edge of said side wall, said first seal element having two, spaced-apart, rail-like projections that extend continuously around said free edge of said side wall; and
   a lid attachable to said tray, said lid having a rigid second seal element thereon, said second seal element includes a continuous, spaced-apart, rail-like projection, said second seal element being dimensioned to matingly engage said first seal element on said tray, said rail-like projection on said lid being disposed between and spaced-apart from two of said rail-like projections on said tray when said lid is attached to said tray, wherein a convoluted path is defined between said first seal element and said second seal element; and
   a fluid passage extending through said side wall and communicating with said convoluted path to direct a microbial deactivation fluid into said path.

2. A container as defined in claim 1, wherein said first seal element is an integral part of said tray, and said second seal element is an integral part of said lid.

3. A container as defined in claim 1, wherein said path defined between said first seal element and said second seal element is generally serpentine in shape.

4. A container as defined in claim 3, wherein said first and said second seal elements are comprised of two spaced-apart rail-like projections.

5. A container as defined in claim 4, wherein said two rail-like projections on said tray abut said lid when said lid is attached to said tray.

6. A container as defined in claim 5, wherein said rail-like projections on said lid do not engage said tray.

7. A container as defined in claim 4, wherein a serpentine path is defined between said rail-like projections on said lid and said rail-like projections on said tray.

8. A container for holding items to be microbially deactivated in a reprocessor having:
   a tray for holding said items to be deactivated,
   a lid operable to cover said tray, said lid and tray defining a cavity to hold said items to be deactivated,
   interacting seal means on said tray and said lid forming a seal between said tray and said lid, said seal means defining a continuous U-shaped channel that provides a convoluted path between said cavity and the exterior of said container, and a fluid passage extending through a wall in said tray and communicating with said U-shaped channel to direct a microbial deactivation fluid into said U-shaped channel.

9. A container as defined in claim 8, wherein said tray has a rigid, first seal element formed therealong and said lid has a rigid, second seal element formed therealong that matingly engages said first seal element on said tray.

10. A container as defined in claim 9, wherein said first seal element is an integral part of said tray and said second seal element is an integral part of said lid.

11. A container as defined in claim 10, wherein said first and second seal elements include interlocking rail-like projections.

12. A container as defined in claim 11, wherein said first and second seal elements each include two, spaced-apart rail-like projections.

13. A container as defined in claim 12, wherein said interlocking rail-like projections define a serpentine path between said cavity and said exterior of said container.

14. A container as defined in claim 13, wherein said tray has a bottom wall and a continuous side wall extending from the periphery of said bottom wall, said side wall having an upper free edge having said rail-like projections formed thereon.

* * * * *